US008421855B2

(12) United States Patent
Buckland et al.

(10) Patent No.: US 8,421,855 B2
(45) Date of Patent: Apr. 16, 2013

(54) OPTICAL COHERENCE TOMOGRAPHY (OCT) IMAGING SYSTEMS FOR USE IN PEDIATRIC OPHTHALMIC APPLICATIONS AND RELATED METHODS AND COMPUTER PROGRAM PRODUCTS

(75) Inventors: Eric L. Buckland, Hickory, NC (US); Robert H. Hart, Cary, NC (US); Glenn A. Myers, Durham, NC (US); Joseph A. Izatt, Raleigh, NC (US)

(73) Assignee: Bioptigen, Inc., Durham, NC (US)

(*) Notice: Subject to any disclaimer, the term of this patent is extended or adjusted under 35 U.S.C. 154(b) by 878 days.

(21) Appl. No.: 12/428,603

(22) Filed: Apr. 23, 2009

(65) Prior Publication Data

US 2009/0268020 A1 Oct. 29, 2009

Related U.S. Application Data

(60) Provisional application No. 61/047,265, filed on Apr. 23, 2008.

(51) Int. Cl.
*A61B 3/10* (2006.01)
*A61B 3/107* (2006.01)
*A61B 5/00* (2006.01)

(52) U.S. Cl.
USPC .............................................. 348/78; 348/77

(58) Field of Classification Search .................... 348/78, 348/77
See application file for complete search history.

(56) References Cited

U.S. PATENT DOCUMENTS 6,053,613 A 4/2000 Wei et al.
6,741,359 B2 5/2004 Wei et al.
7,140,730 B2 11/2006 Wei et al.
7,784,941 B2 * 8/2010 Fukuma et al. ............... 351/205
8,049,899 B2 * 11/2011 Waelti et al. ................. 356/497
2007/0076217 A1 4/2007 Baker et al.
2007/0159595 A1 * 7/2007 Fukuma et al. ............... 351/206

(Continued)

FOREIGN PATENT DOCUMENTS

EP 1 738 680 A1 1/2007
EP 1 806 092 A1 7/2007
WO WO 2007/065670 A2 6/2007
WO WO 2008/052793 A1 5/2008

OTHER PUBLICATIONS

Choma et al., "Sensitivity advantage of swept source and Fourier domain optical coherence tomography," Optics Express, vol. 11, No. 18, pp. 2183-2189, Sep. 8, 2003.

(Continued)

*Primary Examiner* — Kenneth R Coulter
(74) *Attorney, Agent, or Firm* — Myers Bigel Sibley & Sajovec

(57) ABSTRACT

Optical coherence tomography (OCT) imaging systems for imaging an eye are provided including a source having an associated source arm path and a reference arm having an associated reference arm path coupled to the source path, the reference arm path having an associated reference arm path length. A sample having an associated sample arm path coupled to the source arm and reference arm paths is provided. A reference arm path length adjustment module is coupled to the reference arm. The reference arm path length adjustment module is configured to automatically adjust the reference arm path length such that the reference arm path length is based on an eye length of the subject. Related methods and computer program products are also provided.

36 Claims, 18 Drawing Sheets

U.S. PATENT DOCUMENTS

| | | | | |
|---|---|---|---|---|
| 2007/0291277 | A1 | 12/2007 | Everett et al. | |
| 2008/0106696 | A1 | 5/2008 | Buckland | |
| 2009/0268209 | A1 * | 10/2009 | Waelti et al. | 356/479 |

OTHER PUBLICATIONS

Fercher et al., "Measurement of intraocular distances by backscattering spectral interferometry," Optics Communications, vol. 117, pp. 43-48, May 15, 1995.

Tan-no et al., "Optical multimode frequency-domain reflectometer," Optics Letters, vol. 19, No. 8, pp. 587-589, Apr. 15, 1994.

International Search Report, PCT/US2009/002499, Sep. 10, 2009.

Pennie et al., "A longitudinal study of the biometric and refractive changes in full-term infants during the first year of life," Vision Research 41 (2001) 2799-2810.

Ying et al., "Morphoetric Measurements of Fetal and Neonatal Eyes Using MRI and Ultrasound," Neuroembryol Aging 5 (2008) 60-62.

* cited by examiner

OPTICAL COHERENCE TOMOGRAPHY (OCT) IMAGING SYSTEMS FOR USE IN PEDIATRIC OPHTHALMIC APPLICATIONS AND RELATED METHODS AND COMPUTER PROGRAM PRODUCTS

CLAIM OF PRIORITY

The present application claims priority from U.S. Provisional Application No. 61/047,265, filed Apr. 23, 2008, the disclosure of which is hereby incorporated herein by reference as if set forth in its entirety.

STATEMENT OF GOVERNMENT SUPPORT

This invention was made with government support under grant number 2R44EY015585 awarded by National Institutes of Health, National Eye Institute. The United States Government has certain rights in this invention.

FIELD

The present invention relates to imaging and, more particularly, to optical coherence tomography (OCT) and related systems, methods and computer program products.

BACKGROUND

Optical Coherence Tomography (OCT) systems have generally been designed, manufactured and deployed with a target to serve diagnosis of eye disease in the adult population with a mature structure of the eye. Such systems are typically designed with focal optics and interferometric arrangements suitable for imaging the retinal plane, and visualizing and quantifying pathologies related to major eye diseases, such as glaucoma and macular-degeneration. Such systems are used in practice wherever appropriate, but the visibility of pathologies and the quality of images is constrained by design decisions that have been optimized for the distribution of attributes of the adult eye, as eye disease in the majority of cases is demographically associated with increasing age.

A system designed for a mature eye may not be well suited for a broad range of applications. For example, pediatric applications have their own distinct requirements. The pediatric eye, by definition, is a developing eye, and the neonatal eye is considerably smaller than the mature eye. With the increasing incidence of successful births of premature babies, pediatric patients may exhibit a broad range of congenital malformations and genetic disorders, frequently with a dramatic deviation from normal pathology. A premature baby in the neonatal intensive care unit (NICU) may be at risk for a host of chronic diseases, including retinopathy of prematurity, that typically require careful diagnosis and management. Furthermore, in pediatric ophthalmology there is also a high incidence of traumatic damage due to, for example, conditions ranging from shaken-baby syndrome to accidents generally associated with small children.

SUMMARY

Some embodiments of the present invention provide optical coherence tomography (OCT) imaging systems for imaging an eye including a source having an associated source arm path and a reference arm having an associated reference arm path coupled to the source path, the reference arm path having an associated reference arm path length. A sample having an associated sample arm path coupled to the source arm and reference arm paths is provided. A reference arm path length adjustment module is coupled to the reference arm. The reference arm path length adjustment module is configured to automatically adjust the reference arm path length such that the reference arm path length is based on an eye length of the subject.

In further embodiments of the present invention, the reference arm path length may be adjusted to accommodate subject eye lengths in the sample arm ranging from about 2.0 mm to about 50 mm. The reference arm path length may be optimized based on a sample arm optical path length to within a prescribed offset from a focal plane of the OCT system.

In still further embodiments of the present invention, a lens system including at least one lens is provided in the sample arm path and at least one surface of the eye, the lens system having a field curvature that matches a curvature of a retina of the eye of the subject. The at least one lens may be configured to image a mature eye or a pediatric eye. A distance from a cornea to a retina of the mature eye may be about 25 mm and a the distance from the cornea to the retina of the pediatric eye may be from about 14 mm to about 25 mm.

In some embodiments of the present invention, the at least one lens may have an associated focus adjustment that enables imaging into both anterior and posterior regions of the posterior chamber of the eye of the subject. In certain embodiments, the focus adjustment may accommodate at least +30 D of additional focal power. In some embodiments, the focus adjustment may accommodate at least +50 D of additional focal power or up to +100 D of additional focal power.

In further embodiments of the present invention, the system may be a wide field imaging system providing a field of view of about equal to or greater than 50 degrees.

In still further embodiments of the present invention, the system may be a wide field imaging system providing a field of view of about equal to or greater than 140 degrees in combination with rotation about a pupil.

In some embodiments of the present invention, the reference arm path length adjustment module is configured to set a target reference arm path length based on an age of the subject. The reference arm path length adjustment module may be configured to set a target reference arm path length based on additional information pertaining to the subject. The additional information may include a refractive status of the eye of the subject; measured axial eye length of the subject; and/or any relevant test results.

In further embodiments of the present invention, the OCT system may be portable such that the OCT system is provided to the subject where the subject is located. In some embodiments of the present invention, the portable OCT system may be configured to provide imaging to a subject independent of the orientation of the subject. The portable OCT system may be configured to be moved to a location of the subject, unplugged and/or receive new samples without being shutdown.

In still further embodiments of the present invention, the portable OCT system may include a portable handheld OCT probe; a battery backup device associated with the portable handheld probe; and a moveable rack configured to receive the portable handheld probe and/or the battery backup device.

In some embodiments of the present invention, the portable OCT system may further include a fixation target for the subject configured to provide a comfort image to the subject during image acquisition. The fixation target may be configured to provide a continuously variable patient comfort image.

In further embodiments of the present invention, the portable OCT system may be configured to provide a visible light that reflects off a cornea of the eye of the subject to enable accurate positioning of the portable OCT system.

In still further embodiments of the present invention, the portable OCT system may include a video and/or digital fundus camera.

In some embodiments of the present invention, the portable OCT system may further include a foot peddle and/or finger trigger configured to control focus adjustment, reference arm path length adjustment and/or trigger acquisition of an image.

In further embodiments of the present invention, the portable OCT system may be configured to provide two orthogonal images to illustrate pathology of an eye of the subject to facilitate aiming of the portable OCT system during image acquisition.

In still further embodiments of the present invention, the portable OCT system may be configured to continuously acquire images until detection of an image capture trigger is detected; and record a predetermined buffered portion of the acquired image upon detection of the image capture trigger. In certain embodiments, the buffered image comprises the most recent from about 2.0 seconds to about 30 seconds of the acquired image.

In some embodiments of the present invention, the continuously acquired image may be streamed to a non-volatile storage for a predetermined period of time.

In further embodiments of the present invention, the system includes a quality assessing module configured to display an acquired image to an image acquisition technician; trigger adjustment of the reference arm path length and/or focusing of at least one lens in the sample arm based on an assessed quality of the displayed image; and trigger the OCT system to initiate or continue acquisition of the image after adjustments are made.

In still further embodiments of the present invention the OCT system may be configured to acquire an image from an aphakic subject.

In some embodiments of the present invention, the OCT system may be a pediatric OCT system.

Further embodiments of the present invention provide OCT imaging systems for imaging an eye including a source having an associated source arm path and a reference arm having an associated reference arm path coupled to the source path, the reference arm path having an associated reference arm path length. A sample having an associated sample arm path coupled to the source arm and reference arm paths is provided. A lens system having at least one lens in the sample arm path is provided. The lens system has a field curvature based on a curvature of a retina of the eye of the subject Still further embodiments of the present invention provide methods for imaging an eye in an optical coherence tomography (OCT) imaging system including setting a target reference arm path length of the OCT system such that the reference arm path length is based on an eye length of a subject; obtaining additional information about the subject relevant to the target reference arm path length; recalibrating the reference arm path length based on the obtained information; and automatically adjusting the reference arm path length based on the recalibrated reference arm path length.

In some embodiments of the present invention, an image is acquired using the OCT system having the adjusted reference arm path length. The method may further include assessing the image quality of the acquired image; determining if the adjusted reference arm path length is optimum; further adjusting the reference arm path length if it is determined that the adjusted reference arm path length is not optimum; and reacquiring the image using the OCT system having the further adjusted reference arm path length.

In further embodiments of the present invention, the steps of assessing, determining, further adjusting and reacquiring may be repeated until an image having a desired quality is obtained.

In still further embodiments of the present invention, further adjusting is followed by determining if a focus of at least one objective lens of the OCT system is optimum; and adjusting focus position of the at least one objective lens of the OCT system if it is determined that the focus of the at least one objective lens is not optimum, wherein reacquiring the image further comprises reacquiring the image using the OCT system having the further adjusted reference arm path length and the adjusted focus.

Some embodiments of the present invention provide computer program products for imaging an eye in OCT imaging systems including computer readable storage medium having computer readable program code embodied in said medium. The computer readable program code includes computer readable program code configured to set a target reference arm path length of the OCT system such that the reference arm path length is based on an eye length of a subject; computer readable program code configured to obtain additional information about the subject relevant to the target reference arm path length; computer readable program code configured to recalibrate the reference arm path length based on the obtained information; computer readable program code configured to automatically adjust the reference arm path length based on the recalibrated reference arm path length; and computer readable program code configured to acquire an image using the OCT system having the adjusted reference arm path length and display the acquired image on an electronic display associated with the OCT system.

DETAILED DESCRIPTION OF EMBODIMENTS OF THE INVENTION

Figure 1:
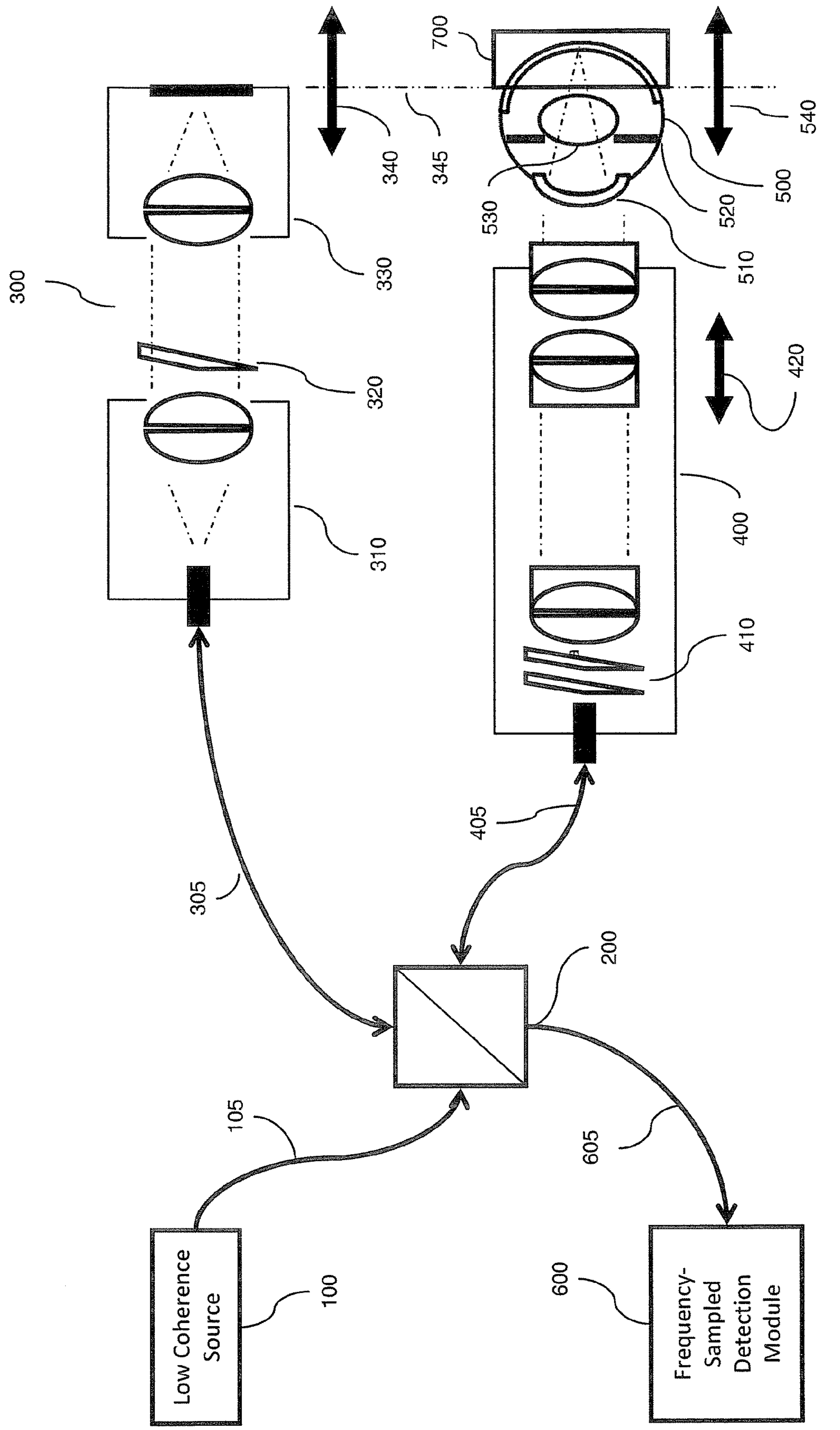
FIG. 1 is a block diagram illustrating a Fourier domain retinal optical coherence tomography system in accordance with some embodiments of the present invention.

The present invention will be described more fully hereinafter with reference to the accompanying figures, in which embodiments of the invention are shown. This invention may, however, be embodied in many alternate forms and should not be construed as limited to the embodiments set forth herein.

Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention as defined by the claims. Like numbers refer to like elements throughout the description of the figures.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising," "includes" and/or "including" when used in this specification, specify the presence of stated features, integers, steps, operations, elements, and/or components, but do not preclude the presence or addition of one or more other features, integers, steps, operations, elements, components, and/or groups thereof. Moreover, when an element is referred to as being "responsive" or "connected" to another element, it can be directly responsive or connected to the other element, or intervening elements may be present. In contrast, when an element is referred to as being "directly responsive" or "directly connected" to another element, there are no intervening elements present. As used herein the term "and/or" includes any and all combinations of one or more of the associated listed items and may be abbreviated as "/".

Unless otherwise defined, all terms (including technical and scientific terms) used herein have the same meaning as commonly understood by one of ordinary skill in the art to which this invention belongs. It will be further understood that terms used herein should be interpreted as having a meaning that is consistent with their meaning in the context of this specification and the relevant art and will not be interpreted in an idealized or overly formal sense unless expressly so defined herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element without departing from the teachings of the disclosure. Although some of the diagrams include arrows on communication paths to show a primary direction of communication, it is to be understood that communication may occur in the opposite direction to the depicted arrows.

Conventional OCT imaging systems are designed to image a mature adult eye. OCT imaging systems directed to the pediatric population will typically require specific optics for the pre-adolescent eye, an increased dynamic range of performance attributes including field of view, focal adjustments, and interferometric path length matching conditions and the like. However, the pediatric patient is not well suited to a standard clinical imaging system designed for the mature adult eye. Accordingly, an imaging system that is directed to a smaller, uncooperative patient, whether in the clinic or in the operating suite, may be desired for more accurate, successful imaging.

Thus, some embodiments of the present invention provide a coherence-gated imaging system (optical coherence tomography (OCT) system) that provides high resolution depth-resolved images of retinal pathologies over a broad field of view in patients with eyes ranging from the premature underdeveloped eye to the fully developed eye, with adjustment capabilities to observe disease, trauma, and malformations, in environments from the clinic, to the operating suite, to the field and the like as will be discussed further below with respect to FIGS. 1 through 20.

In particular, some embodiments of the present invention provide an OCT system, for example, a Spectral Domain (SD) OCT system, specifically designed for pediatric patients is described. As discussed herein, OCT systems in accordance with some embodiments of the present invention include an electromechanical mechanism to manually or automatically adjust a reference arm path length. The OCT system is configured to estimate an initial reference arm path length (axial length) based on information such as the age of the patient, refractive status of the patient's eye and the like. The OCT delivery optics (i.e. the patient interface) include lenses with a relatively larger field of view than provided by conventional systems, which may enable examination of the entire retina including the periphery. Furthermore, the small physical size of the final stage of these lenses may allow a portable OCT system in accordance with some embodiments of the present invention to be aimed widely within the patient's orbit.

Referring first to FIG. 1, a block diagram illustrating a Fourier domain retinal OCT system in accordance with some embodiments of the present invention will be discussed. As illustrated in FIG. 1, the system includes a low coherence source 100, a reference arm 300 and a sample arm 400 coupled to each other by a beamsplitter 200. The beamsplitter 200 may be, for example, a fiber optic coupler or a bulk or micro-optic coupler without departing from the scope of the present invention. In some embodiments, the beamsplitter 200 may provide from about a 50/50 to about a 90/10 split ratio, with the larger fractional power directed to the reference arm path. As further illustrated in FIG. 1, the beamsplitter 200 is also coupled to a frequency sampled detection module 600 over a path 605 that may be provided by an optical fiber.

As further illustrated in FIG. 1, the source 100 is coupled to the beamsplitter 200 by a source path 105. The source 100 may be, for example, an SLED or tunable source. The reference arm 300 is coupled to the beamsplitter over a reference arm path 305. Similarly, the sample arm 400 is coupled to the beamsplitter 200 over the sample arm path 405. In some embodiments of the present invention, the source path 105, the reference arm path 305 and the sample arm path 405 may all be provided by optical fiber.

In accordance with some embodiment of the present invention, the reference arm 300 further includes a collimator assembly 310, a variable attenuator 320 that can be neutral density or variable aperture, a mirror assembly 330, a reference arm variable path length adjustment 340 and a path length matching position 345, i.e. optical path length reference to the eye 500. As further illustrated, the sample arm 400 according to some embodiments of the present invention may include a dual-axis scanner assembly 410 and an objective lens variable focus 420.

The sample in FIG. 1 is an eye 500 including a cornea 510, iris/pupil 520, ocular lens 530 and eye length 540. As will be discussed in detail herein, the eye length 540 in accordance with some embodiments of the present invention may be a subject specific, age dependent, pathology dependent axial optical eye length.

As further illustrated in FIG. 1, a representation of an OCT imaging window 700 is illustrated near the eye 500. The OCT imaging window is the depth over which the SD-OCT system provides an image. The window depth is well-known to be a function of the sampling interval of the spectral interferogram. The window depth is measured from the position 345 in the sample arm path at which the optical path length matches the reference arm optical path length. An image may be acquired for sample positions greater than or less than the reference arm path length, such selection is a function of operator choice and software image processing algorithms.

OCT systems in accordance with some embodiments of the present invention are configured with a reference arm path length adjustment module 340. The reference arm path length adjustment module may include any combination of the collimator assembly 310, the variable attenuator 320, the mirror assembly 330, the reference arm variable path length adjustment 340 and the path length matching position 345 of the reference arm 300 discussed above. In particular, the reference arm path length adjustment module 340 is configured to manually or automatically adjust the reference arm path length such that the reference arm path length is based on an eye length of the subject 540. The presence of this module allows the OCT system to adjust to patients having different eye lengths 540, thus allowing eyes of patients having immature eyes (pediatric patients), for example, eyes having a length of less than 25 mm, to be accurately imaged. Eye length is measured as the distance between the cornea 510 and the retina. A mature adult eye typically has a length of about 25 mm and a pediatric eye length can be from about 14 mm to about 25 mm. Accordingly, the reference arm path length adjustment module in accordance with some embodiments of the present invention may be made capable to accommodate eye lengths ranging from about 10 mm to about 30 mm, and preferable to accommodate eye lengths ranging from about 2 mm to about 50 mm, to accommodate fetal development and the mature eye of larger animal models. The reference arm optical path length may be optimized to correspond with a prescribed range of offsets to a sample arm optical path length as measured to a focal plane of the OCT system. The reference arm path length may generally be selected to be offset from the sample arm path length as measured to a focal plane of the OCT imaging system with a range of 0 mm to 2 mm, and may be less than or greater than the corresponding sample arm path length.

In some embodiments of the present invention, the reference arm path length adjustment module is configured to set a target reference arm path length based on an age of the subject and/or a refractive status of the eye of the subject. The target reference arm path length may be set using the patient's age and a standard table for the growth of an eye. Such a table may be found in, for example, *A longitudinal study of the biometric and refractive changes in full-term infants during the first year of life* by Pennie et al, Vision Research 41 (2001, 2799-2810). This target reference arm path length may then be fine tuned based on additional information pertaining to the subject that may be obtained, for example, the patient's actual measured eye length, ultrasound results or other relevant test results. The reference arm path length may then be adjusted based on this additional information to provide a more accurate OCT image.

As discussed above, OCT systems in accordance with some embodiments of the present invention may further include at least one lens in the sample arm path 405 (scanner assembly 410) such that the at least one lens in combination with the optical attributes of the subject eye has a field curvature that matches a curvature of a retina of the eye of the subject. In other words, the lenses may be switched to conform to the eye length, for example, 25 mm or 14 mm, of the patient. Thus, OCT systems discussed herein can be configured to image both a mature eye and a pediatric eye. OCT systems in accordance with some embodiments of the present invention provide a wide field imaging system providing a field of view of up to about 50 degrees. In combination with rotation around the pupil of the eye, the pediatric lens provides a field of view of 140 degrees.

As discussed above, the scanner assembly 410 including the at least one lens has an associated focus adjustment provided by, for example, the objective lens variable focus 420, that enables imaging into both anterior and posterior regions of the posterior chamber of the eye of the subject. Conventional systems do adjust for normal refractive errors in an adult population. Such adult-oriented systems have focal adjustment over the range of +−12 Diopters, to a maximum of +−20 Diopters. It is more critical in the pediatric population to provide optics that can accommodate the range of congenital and traumatic pathologies of this population. Such pathologies include blastomas, requiring increased optical power to focus above the retina as much as 3 to 4 mm, and aphakia (lack of ocular lens), requiring increased optical power to overcome the lack of an ocular lens. In the most extreme case of an aphakic child with a severe blastoma or calcification, such that it is desirable to image as far forward as the posterior plane of the iris, +110 Diopters of focal power are required.

Some embodiments of the present invention may provide lens that allow acquisition of an image from an aphakic patient, i.e. a subject that does not have an ocular lens in the eye or to image a patient with a blastoma or calcification on or above the retina of the eye. The lens of the present invention has a focal range from −12 Diopters to +50 Diopters, with an option to increase the power to +100 Diopters by increasing the zoom and decreasing the working distance to the subject. The reference arm must be adjusted to accommodate the effective reduction in sample optical path length accordingly.

Standard imaging systems are fixed in a single location and, therefore, patients must be brought to the imaging system. As one can imagine, some patients cannot be brought to the system and, therefore, these patients may not be provided with accurate images on which to make a diagnosis. Accordingly, in accordance with some embodiments of the present invention, the OCT system is portable such that the OCT the system is provided to the subject where the subject is located. Thus, portable OCT systems in accordance with some embodiments of the present invention may be moved to a location of the subject, unplugged and/or receive new samples without being shutdown.

Figure 9:
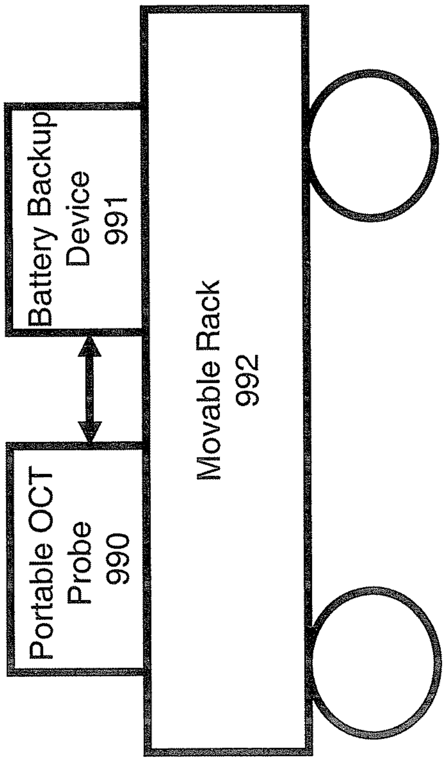
FIG. 9 is a block diagram illustrating a portable OCT system in accordance with some embodiments of the present invention.

As illustrated in FIG. 9, portable OCT systems in accordance with some embodiments of the present invention may include a portable handheld OCT probe 990, which will be discussed further below with respect to FIG. 12, a battery backup device 991 associated with the portable handheld probe, such as a uninterruptible power supply (UPS), and a moveable rack 992 configured to receive the portable handheld probe and/or the battery backup device.

Figure 13:
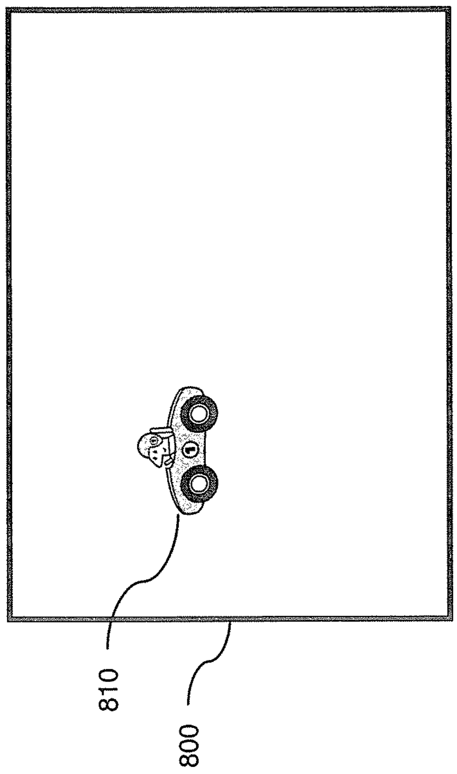
FIG. 13 is a diagram of an exemplary fixation target and excitation source in accordance with some embodiments of the present invention.

The portable OCT system may further include a fixation target for the subject as illustrated in FIG. 13. As illustrated in FIG. 13, a continuous dynamic fixation target and excitation source featuring a liquid crystal display (LCD), organic light emitting diode (OLED) displays, scanning or projection microdisplays, and animated targets for patient comfort will be discussed. In particular, a fixation display 800 associated with the portable OCT system may include a dynamic fixation icon 810 configured to provide a comfort image to the subject during image acquisition. In some embodiments, the fixation target (icon) 810 is configured to provide a continuously variable patient comfort image.

The provision of the fixation target 810 may allow a pediatric patient who is awake during image acquisition to relax and, thus, enabling acquisition of a more accurate image. The fixation target 810 may be any patient comfort image, such as a static or animate cartoon character or icon, without departing from the scope of the present invention.

Portable OCT systems in accordance with some embodiments of the present invention may also provide visible light that reflects off the cornea of the eye of the subject to enable accurate positioning of the portable OCT system. In some embodiments, the portable OCT system may include a video and/or digital fundus camera as discussed further below. In some embodiments, the portable OCT system further includes a foot peddle and/or finger trigger configured to control focus adjustment, reference arm path length adjustment and/or trigger acquisition of an image. In still further embodiments of the present invention, the portable OCT system may further include a foot peddle and/or finger trigger configured to control the OCT source power, attenuation of OCT signal power in the reference arm path, the power of the illumination for the video or digital fundus camera.

Images may be acquired using the portable OCT system using many methods. For example, the portable OCT system may provide two synchronous images to illustrate orthogonal pathology of an eye of the subject to facilitate aiming of the portable OCT system during image acquisition. In other words, the device may be aimed at the portion of the eye to be imaged, present images of nasal-temporal (horizontal) physiology side-by-side with images of inferior-superior (vertical) physiology and acquired by pushing a capture button on the device.

In some embodiments, the portable OCT system may be configured to acquire, process and display images until an image capture button is activated at which point a most recent portion of the acquired image is stored in a buffer having a predetermined size. In some embodiments, the buffered image may include the most recent from about 2.0 seconds to about 30 seconds of the acquired image. In certain embodiments, the continuously acquired image may be streamed to non-volatile memory in a first-in, first-out fashion for a predetermined period of time, such that, for example, a half hour or more of streaming image may be captured.

Some OCT systems according to embodiments of the present invention provide a quality-assessment module configured to provide a figure of merit for the quality of an acquired image. In particular, the quality assessment module is configured to display a figure of merit of an image acquisition technician, trigger adjustment of the reference arm path length and or focusing of at least one lens in the sample arm based on an assessed quality of the displayed image and trigger the OCT system to initiate or continue acquisition of the image after adjustments are made. The figure of merit may be a measure of brightness of the image, and may be computed numerically and compared against a baseline of the system, or may be assessed qualitatively by the photographer.

Accordingly, systems according to some embodiments of the present invention are configured to optimize placement of reference path matching system to within a prescribed distance of a focal plane of the optical system. In other words, OCT systems discussed herein are configured to focus on the correct place in the eye/sample and match the path length to the subject retina or other target physiology or pathology. Thus, some embodiments of the present invention provide methods of providing path matching conditions coordinated to focal conditions for target surfaces. This is in contrast to conventional systems where adjustments to the reference arm path length are made to make minor corrections to a position of an image on a screen, but are not made to coordinate subject eye length, focus and optimum position of reference arm length. As discussed above, conventional systems are designed for a mature eye having a path length of about 25 mm.

In particular, the pediatric population and adult population experience drastically different problems with their eyes. Pediatric patients have typically suffered a trauma or have a congenital malformation that are well away from the retinal plane typically imaged in adult patients. Accordingly, as discussed above, some embodiments of the present invention provide variable reference arm path lengths and adjustable objective lens focusing that allow imaging of portions of the eye more relevant to pediatric patients. Conventional systems do not provide for imaging of pediatric (immature) eyes having eye lengths of less than about 25 mm. Accordingly, some embodiments of the present invention provide a much needed pediatric OCT system as discussed herein.

Figure 2:
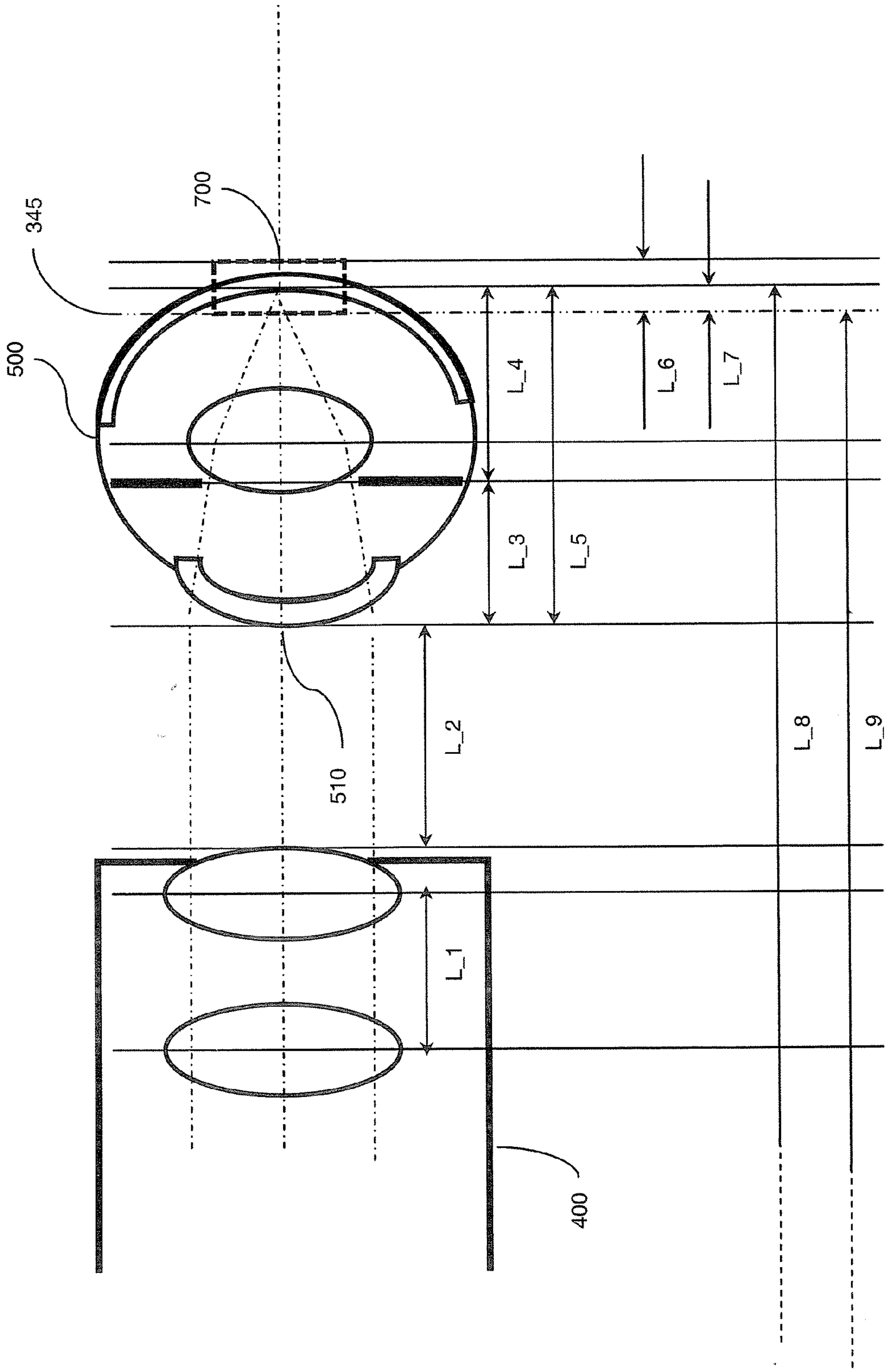
FIG. 2 is a block diagram illustrating a lens configuration for Emmetropic telecentric retinal imaging in accordance with some embodiments of the present invention.
Figure 3:
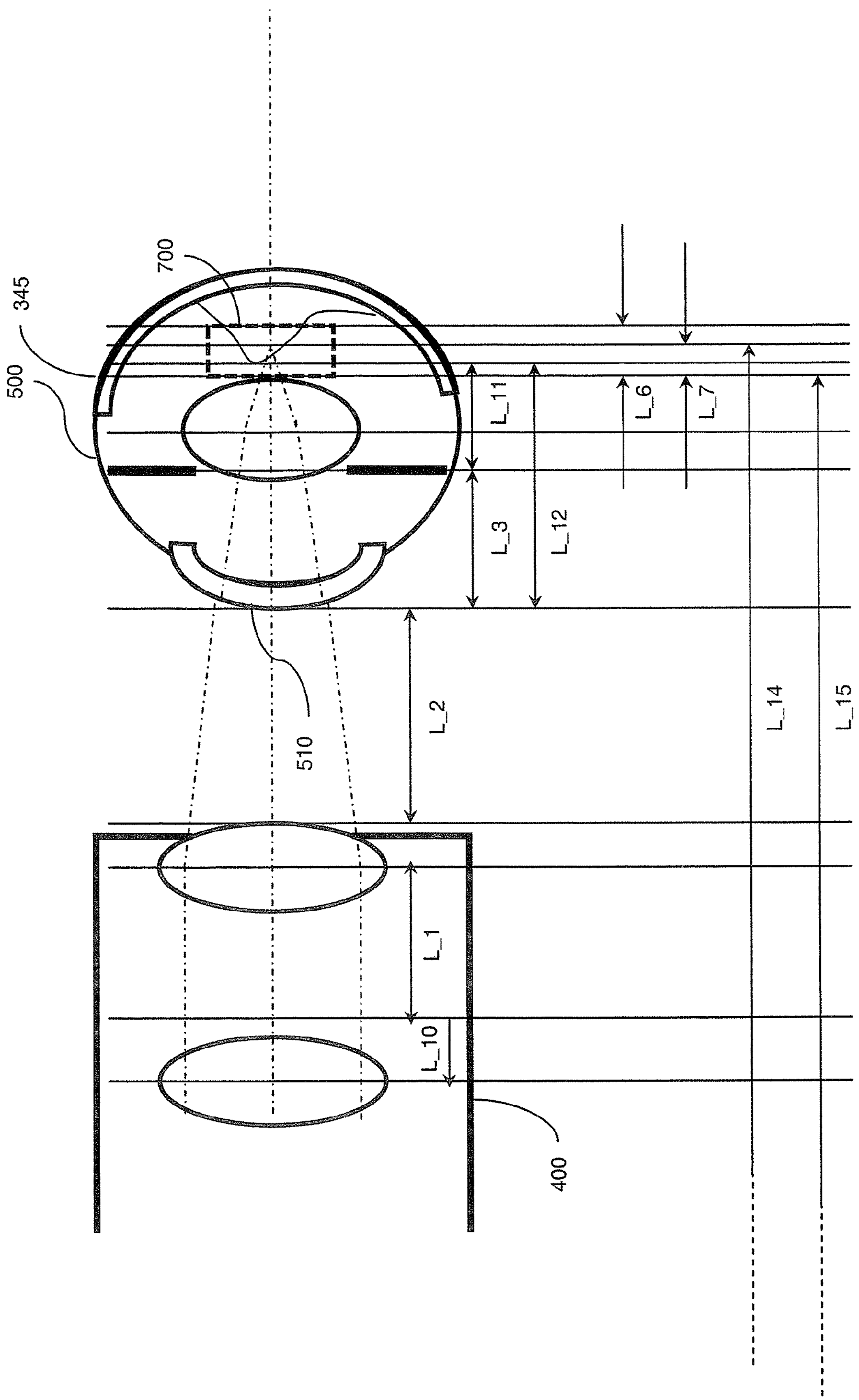
FIG. 3 is a block diagram illustrating a lens configuration for a hyper-focal retinal imaging for blastoma imaging in accordance with some embodiments of the present invention.
Figure 4:
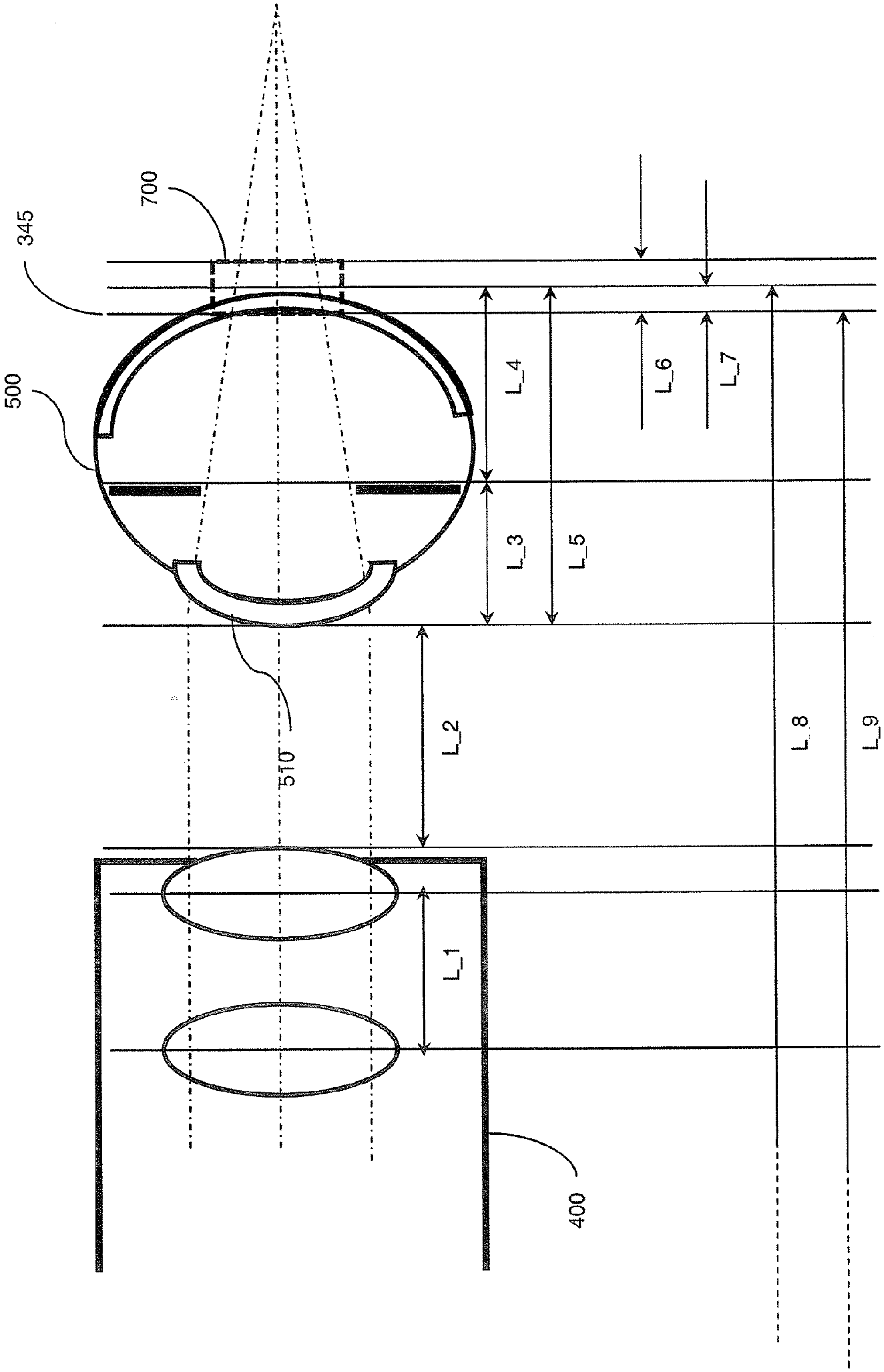
FIG. 4 is a block diagram illustrating a lens configuration for a hypo-focal retinal imaging for aphakia without system accommodation in accordance with some embodiments of the present invention.
Figure 5:
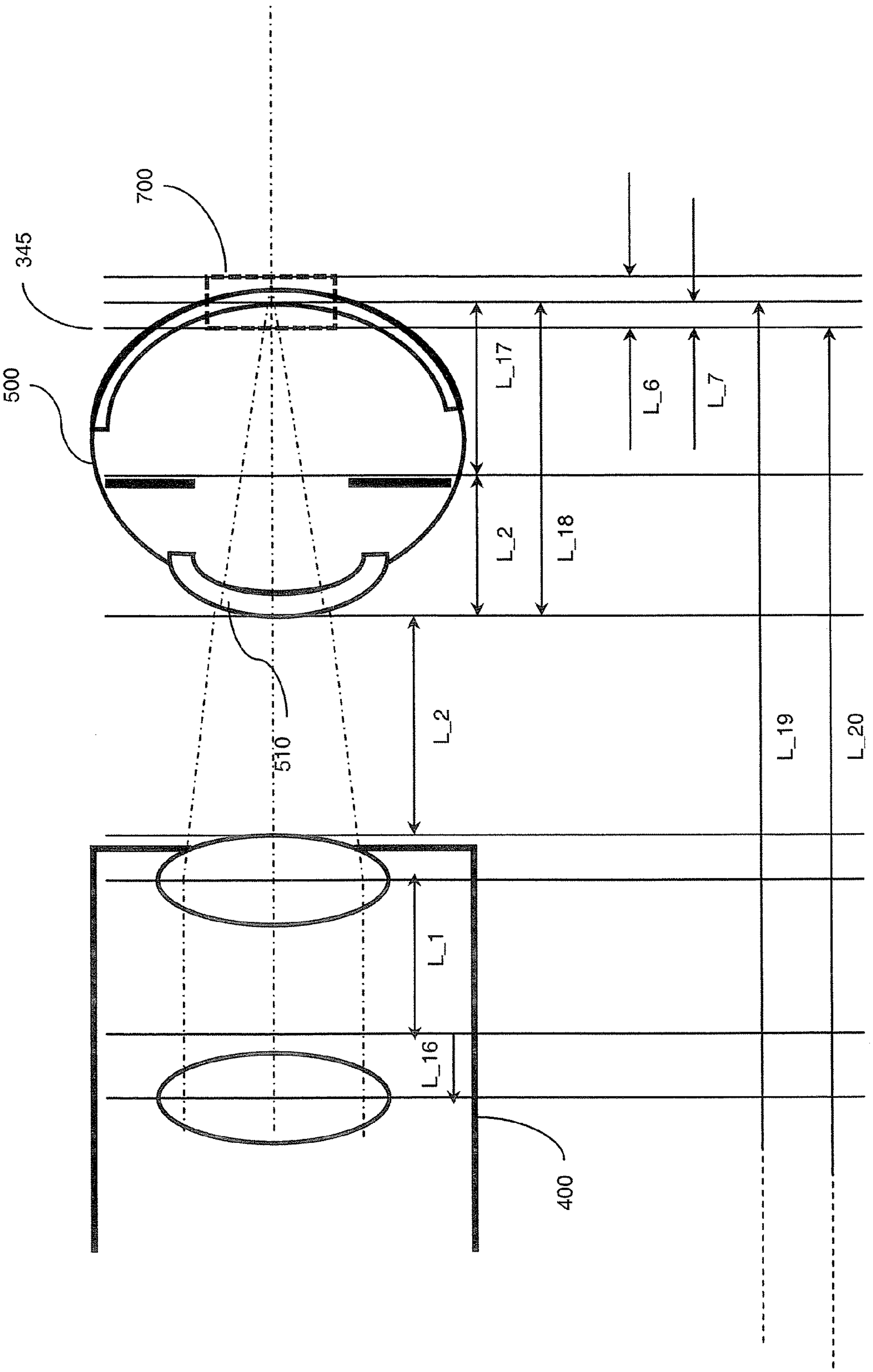
FIG. 5 is a block diagram illustrating a lens configuration for hypo retinal imaging aphakia with system accommodation in accordance with some embodiments of the present invention.
Figure 6:
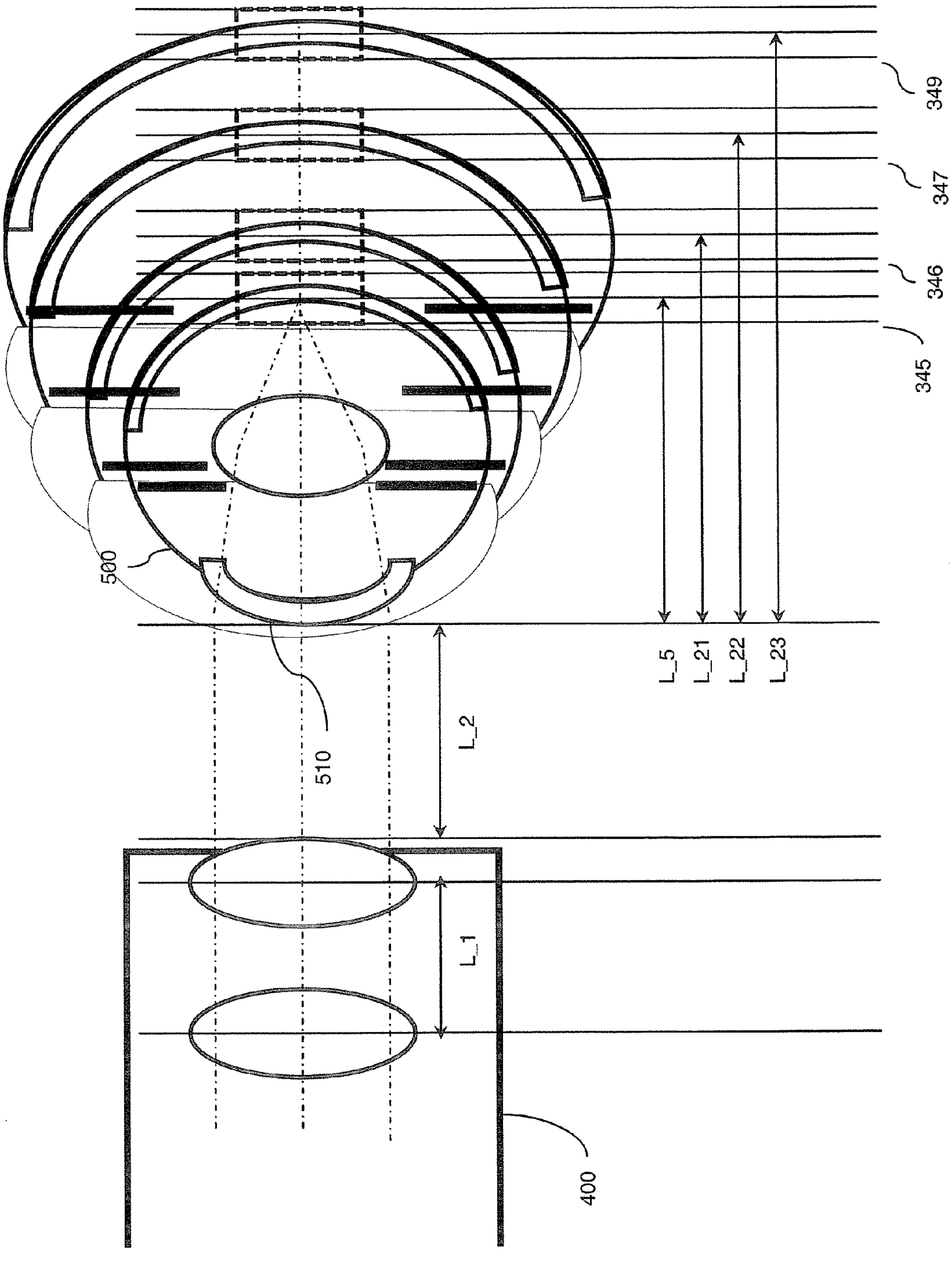
FIG. 6 is a block diagram illustrating a lens configuration for retinal imaging, with system accommodation for varying developmental eye lengths in accordance with some embodiments of the present invention.
Figure 7:
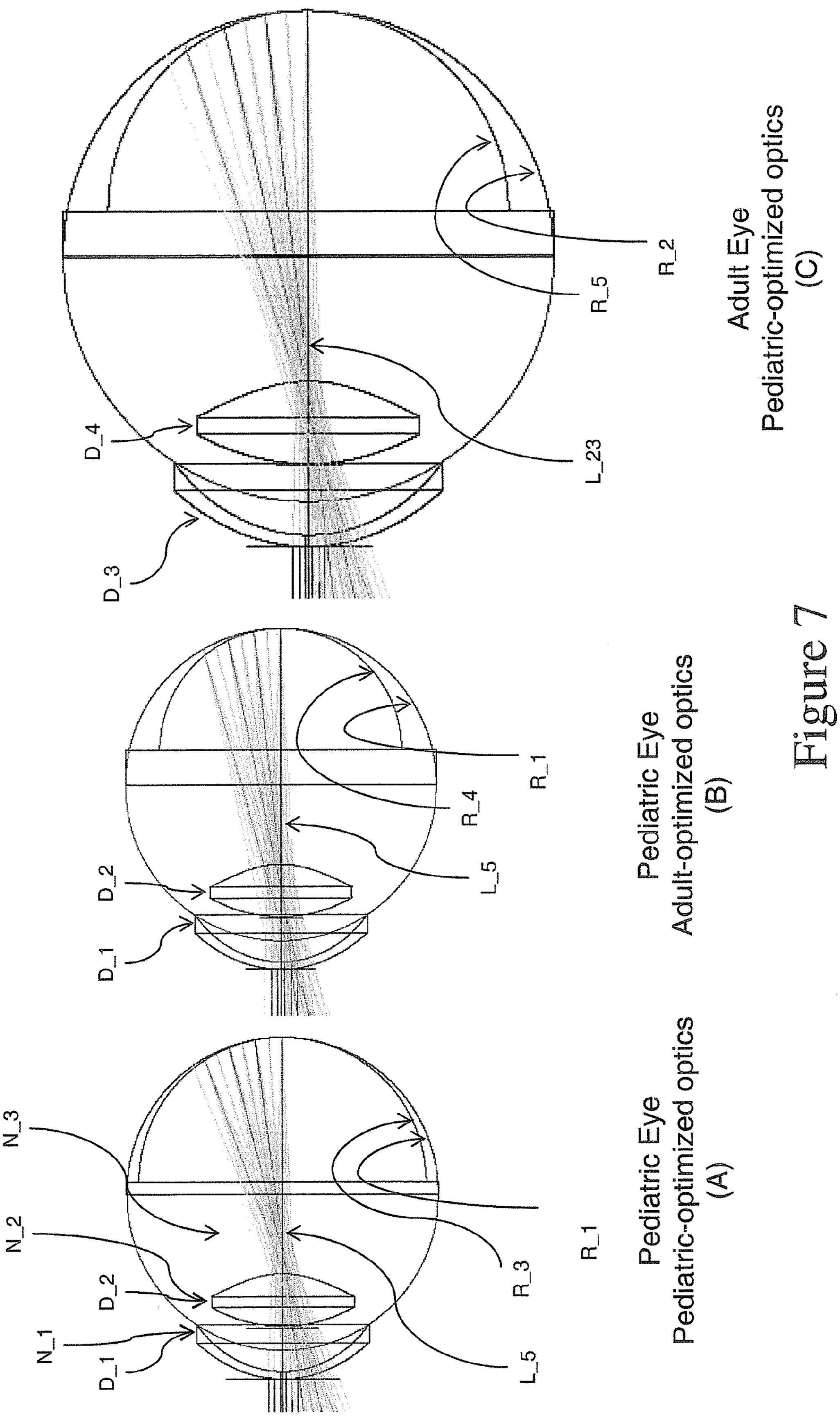
FIGS. 7A through 7C are diagrams illustrating focal field curvature optimization to posterior pole radius of curvature in accordance with some embodiments of the present invention.

Referring now to FIGS. 2 through 6, lens configurations for various retinal imaging in accordance with various embodiments of the present invention will be discussed. FIG. 2 illustrates a lens configuration for Emmetropic telecentric retinal imaging in accordance with some embodiments of the present invention. FIG. 3 illustrates a lens configuration for a hyper-focal retinal imaging for blastoma imaging in accordance with some embodiments of the present invention. FIG. 4 illustrates a lens configuration for a Hypo-focal retinal imaging for aphakia without system accommodation in accordance with some embodiments of the present invention. FIG. 5 illustrates a lens configuration for hypo retinal imaging aphakia with system accommodation in accordance with some embodiments of the present invention. FIG. 6 illustrates a lens configuration for retinal imaging, system with accommodation for varying developmental eye lengths in accordance with some embodiments of the present invention.

Some or all of the following measurements are relevant to the lens configurations of FIGS. 2 through 6 as illustrated thereon. L_1 is the telecentric objective lens separation; L_2 is the working distance from the lens to cornea 510; L_3 is the anterior eye length; L_4 is the posterior eye length; L_5 is the axial eye length (L_5=L_3+L_4); L_6 is the SDOCT imaging window depth; L_7 is the offset between path length matched condition and focus (|L_7|=|L_8−L_9|); L_8 is the sample arm optical path length (to focal beam waist); L_9 is the reference arm optical path length; L_10 is the change in objective lens separation L_1 for change in focusing power; L_11 is the effective posterior eye length to subject pathology; L_12 is the effective axial eye length (L_12=L_3+L_11); L_14 is the sample arm optical path length for hyper-focal imaging; and L_15 is adjusted reference arm optical path length for hyper-focal imaging. A zoom range L_1 enables a focal power of +100 Diopters.

Using these values in accordance with some embodiments of the present invention, Δref is the change in reference arm optical path length L_i−L_9, for example, L_15−L_9 for emmetropic-to-hyper-focal imaging. Δsamp is the change in sample arm optical path length L_j−L_8, for example, L_14−L_8 for emmetropic-to-hyper-focal imaging. |Δref−Δsamp|=ε,ε<L_6 is the change in reference arm and sample arm length. This change need not be precisely equal but will be unequal by only a small amount ε that is less than the SDOCT window depth.

Referring now to FIG. 6, a lens configuration for a retinal imaging system accommodating for varying developmental eye lengths is illustrated therein. L_21 is the adjusted reference arm optical path length for a maturing eye, arbitrary developmental age 1. L_22 is the adjusted reference arm optical path length for a maturing eye, arbitrary developmental age 2. L_23 is the adjusted reference arm optical path length for a mature eye.

Figures 7A, 7B, 7C:
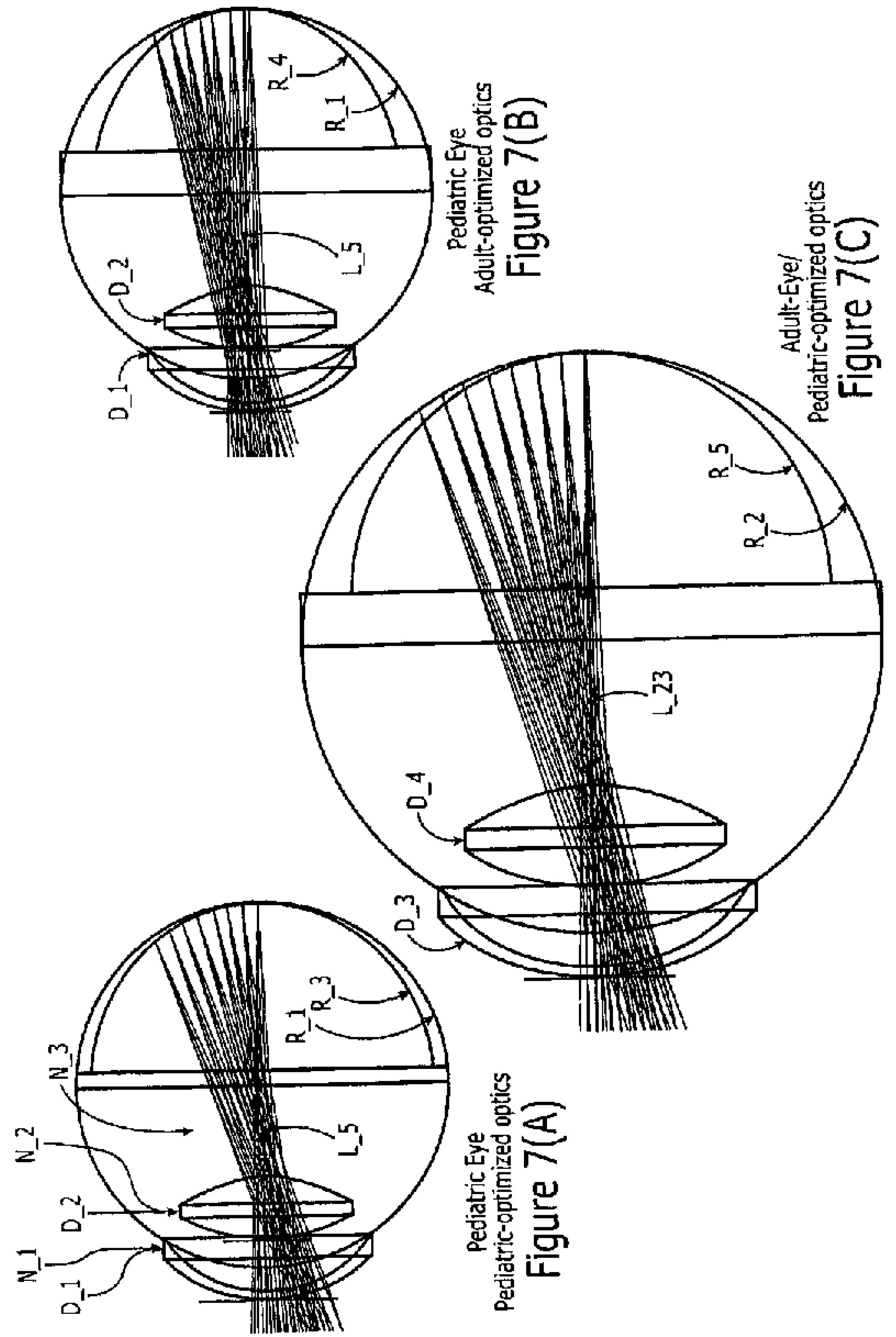
Figure 8:
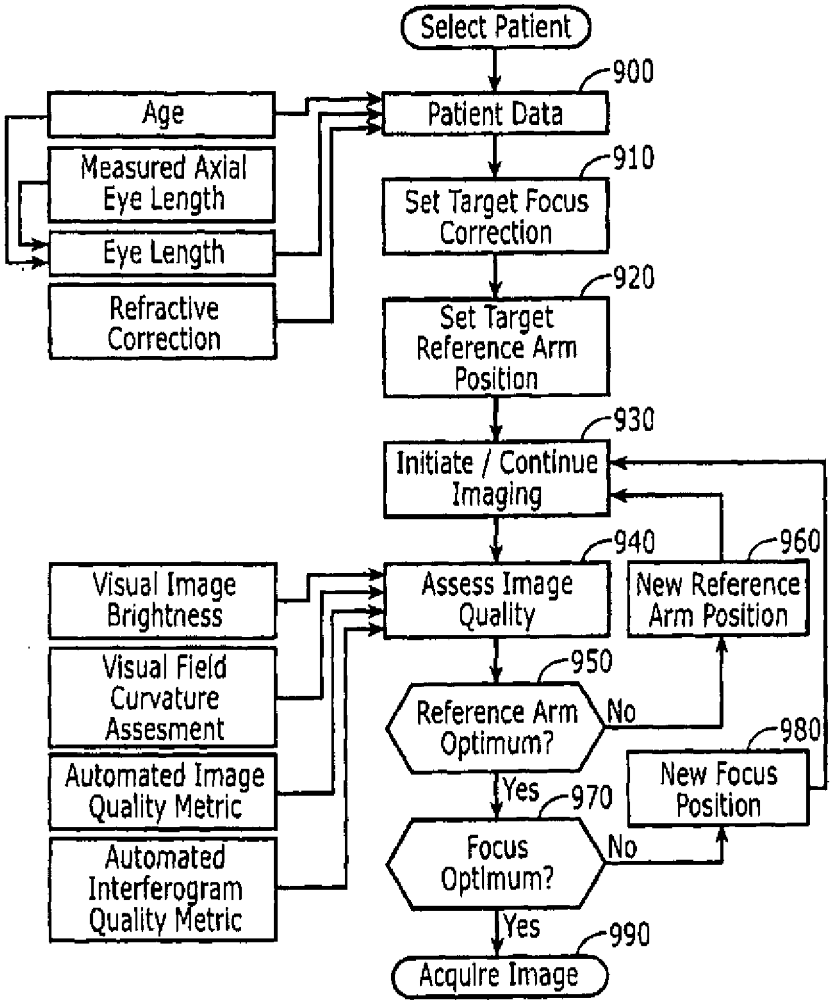
Figure 9:
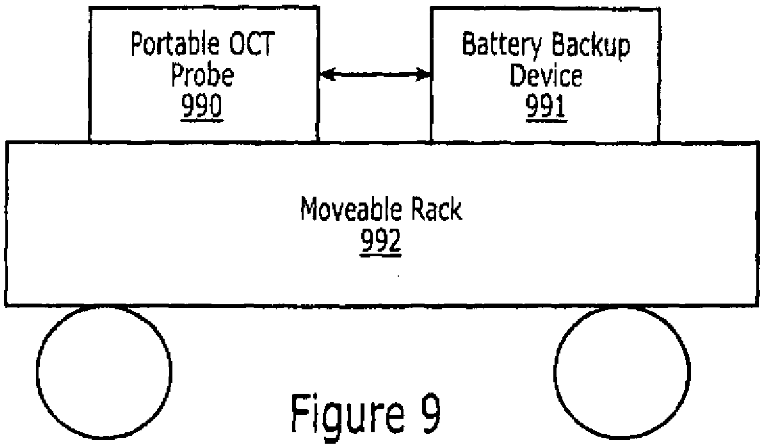
Figure 10:
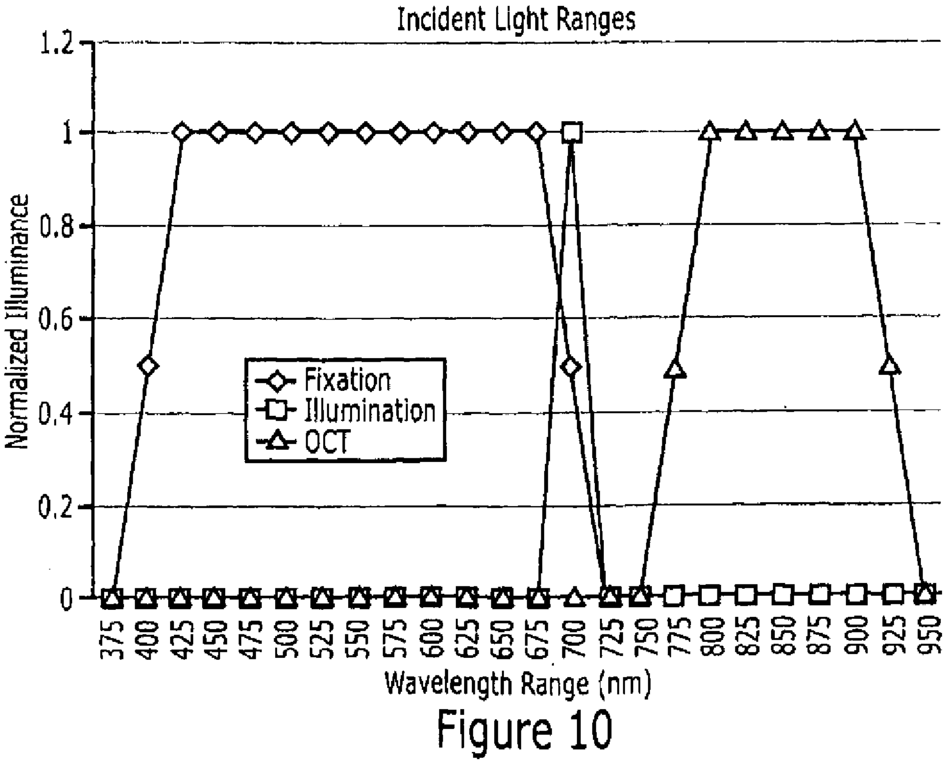
Figure 11:
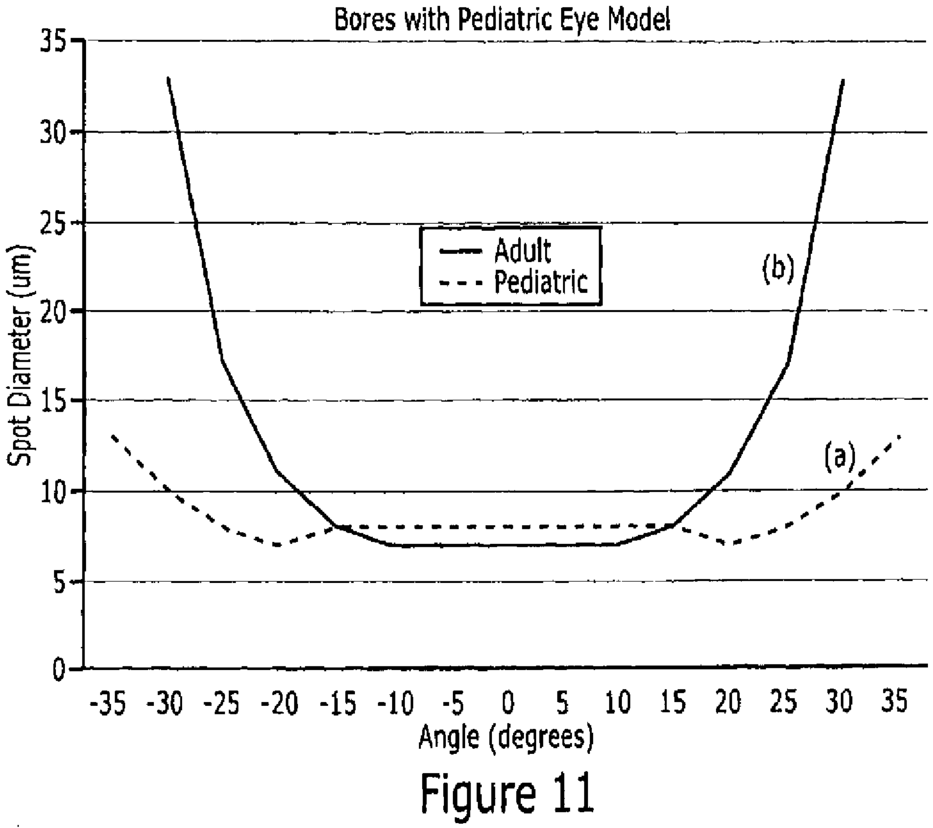
Figure 12:
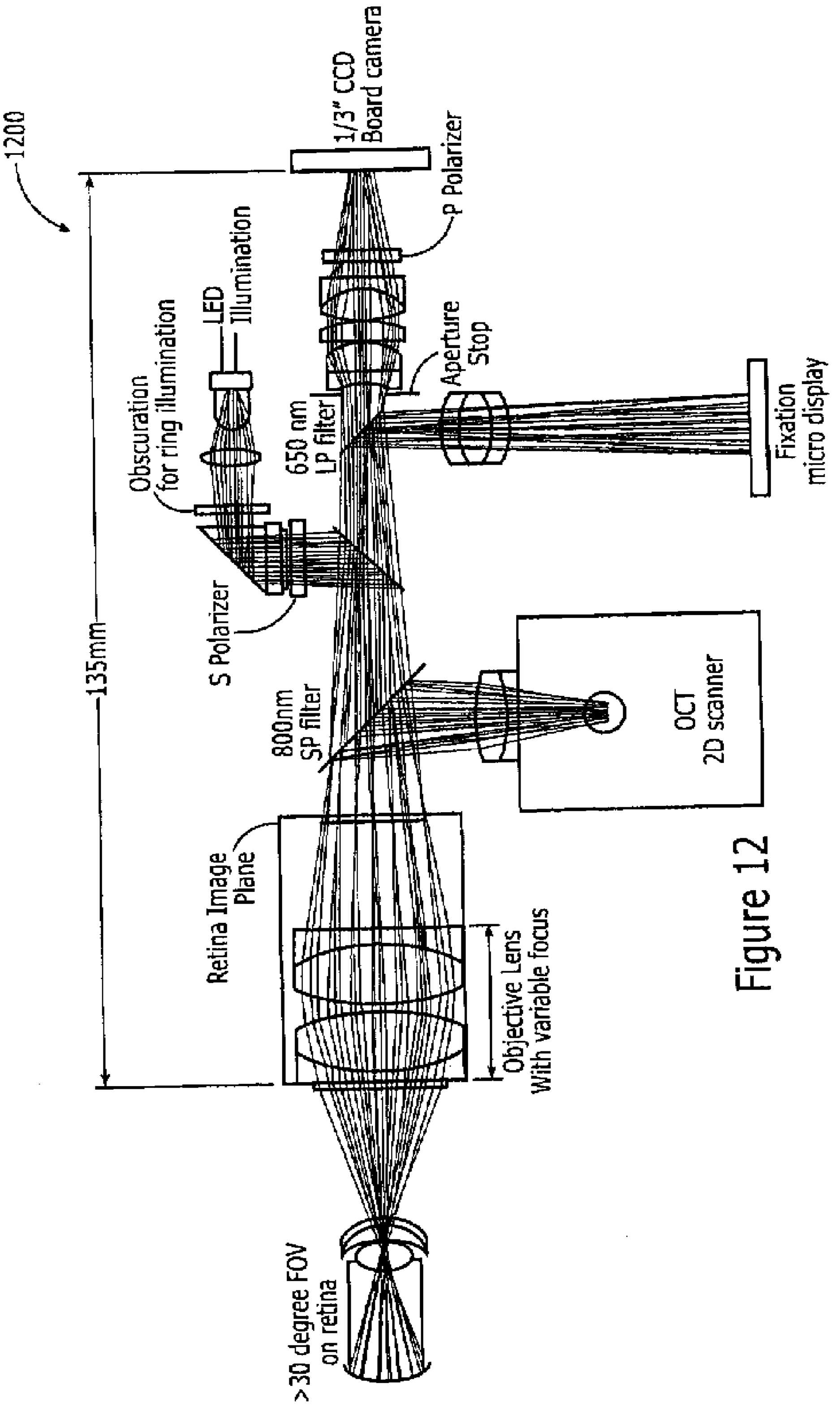
Figure 13:
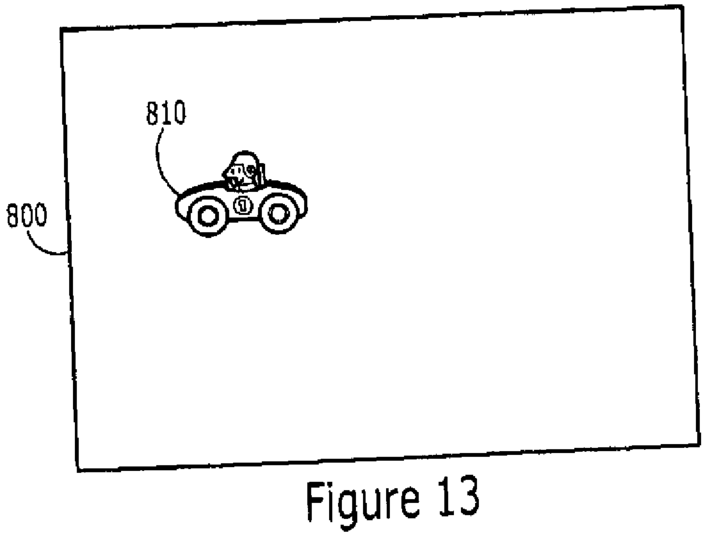
Figure 14:
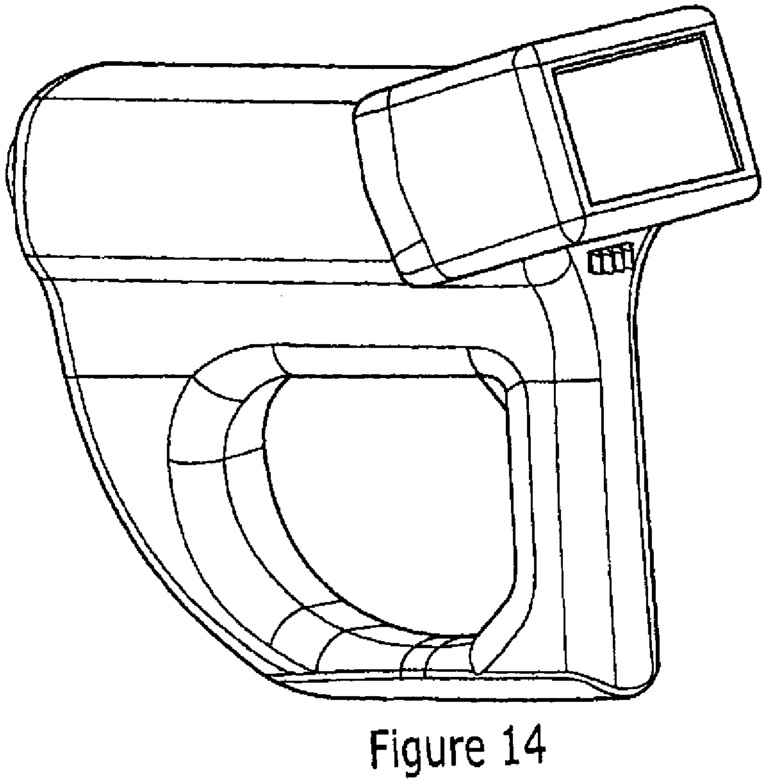
Figure 15:
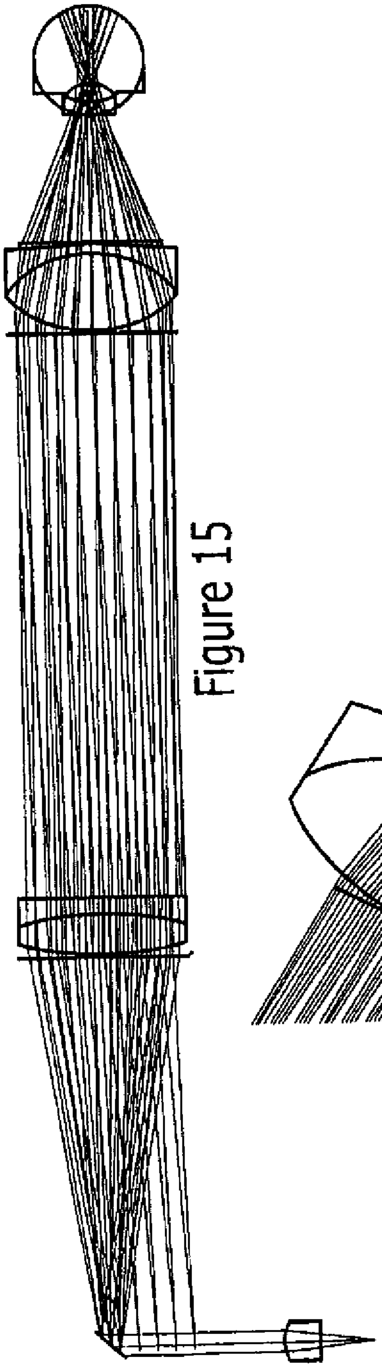
Figure 16:
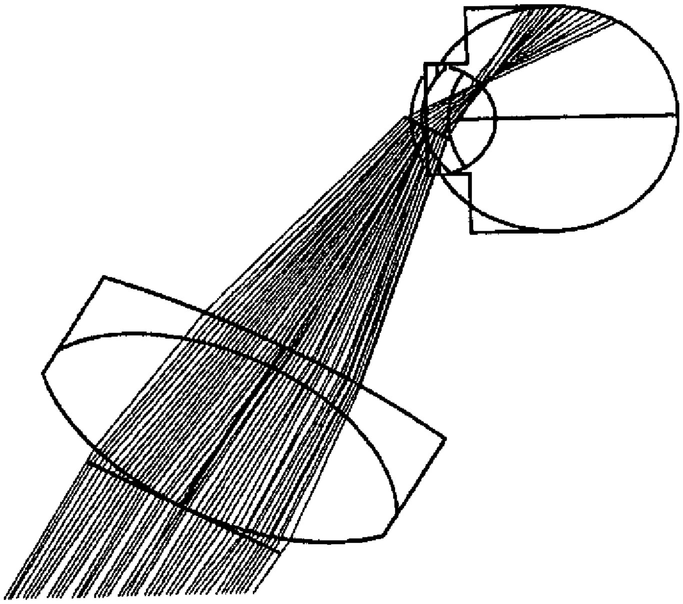
Figure 17:
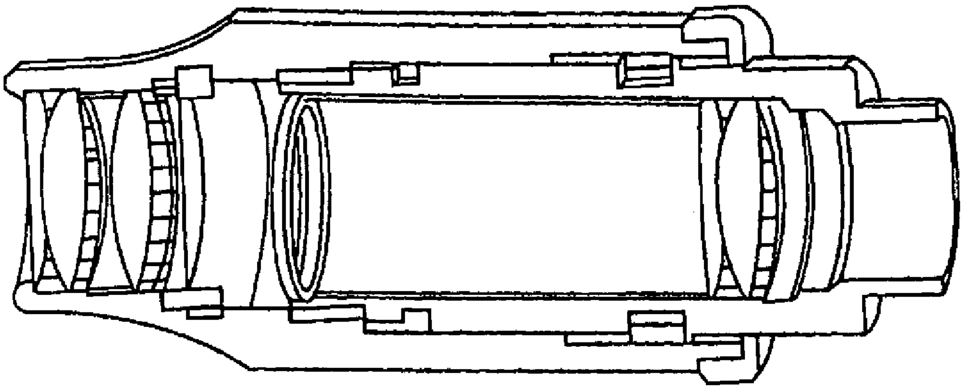
Figure 18:
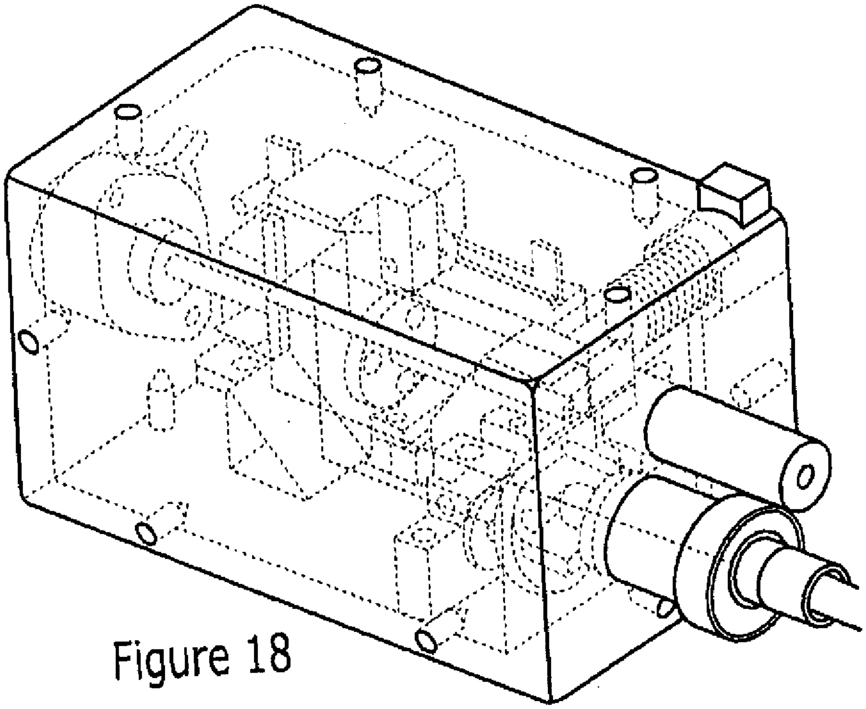
Figure 20:
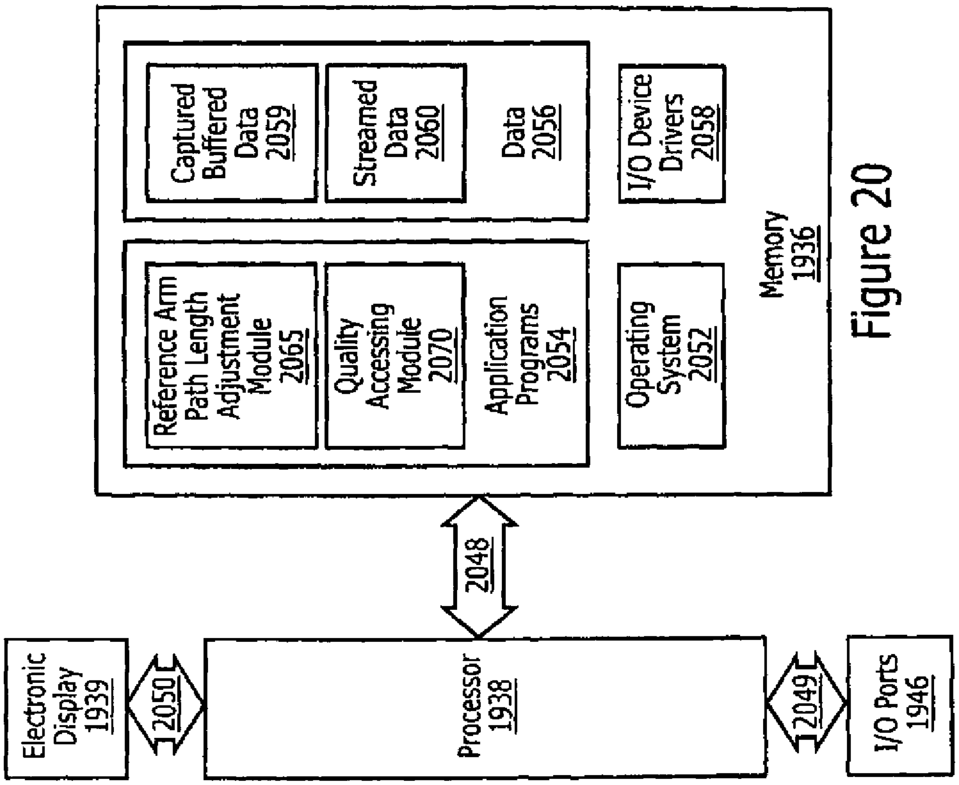
Figure 19:
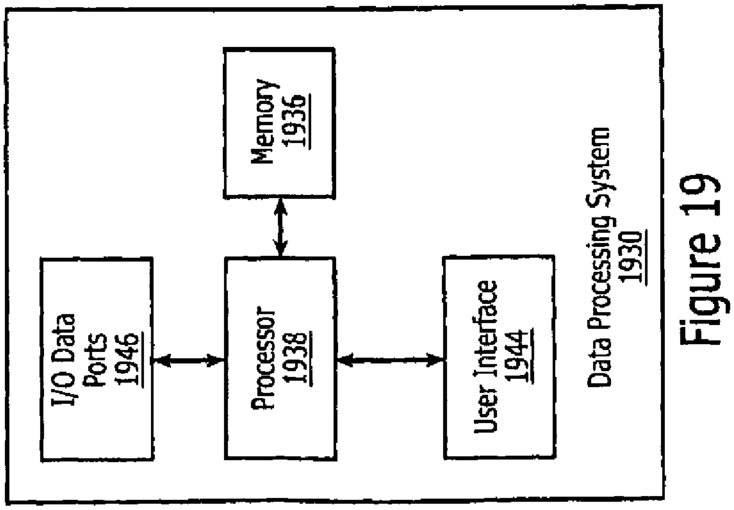

Referring now to FIGS. 7A through 7C, diagrams illustrating Focal field curvature optimization to posterior pole radius of curvature in accordance with some embodiments of the present invention will be discussed. The following values are relevant to the values illustrated in FIGS. 7A through 7C. D_1 is the optical power of pediatric cornea; D_2 is the optical power of pediatric lens; D_3 is the optical power of adult cornea; D_4 is the optical power of adult lens; L_5 is the pediatric axial eye length (optical length); L_23 is the adult axial eye length (optical length); R_1 is the radius of curvature of pediatric posterior pole; R_2 is the radius of curvature of adult posterior pole; R_3 is the field curvature of pediatric imaging optic at pediatric posterior pole; R_4 is the field radius of curvature of adult imaging optic at pediatric posterior pole; R_5 is the field radius of curvature of pediatric imaging optic at adult posterior pole; N_1 is the refractive index of cornea; N_2 is the refractive index of lens; N_3 is the refractive index of vitreous humor; <N> is the effective (path-averaged) refractive index of eye. Furthermore, representative values are as follows D_1 is 60 Diopters; D_2 is 30 Diopters; D_3 is 43 Diopters; D_4 is 21 Diopters; L_5 is 20 mm; L_23 is 34 mm; R_1 is 7 mm; R_2 is 12 mm; R_3 is 7 mm; R_4 is 6 mm; R_5 is 9 mm; N_1 is 1.38; N_2 is 1.57; N_3 1.33 and <N> is 1.37.

Taking these values into account, FIG. 7A illustrates a pediatric eye using pediatric optimized optics in the OCT system; FIG. 7B illustrates a pediatric eye using adult optimized optics in the OCT system; and FIG. 7C illustrates an adult eye using pediatric optimized optics in the OCT system.

Figure 8:
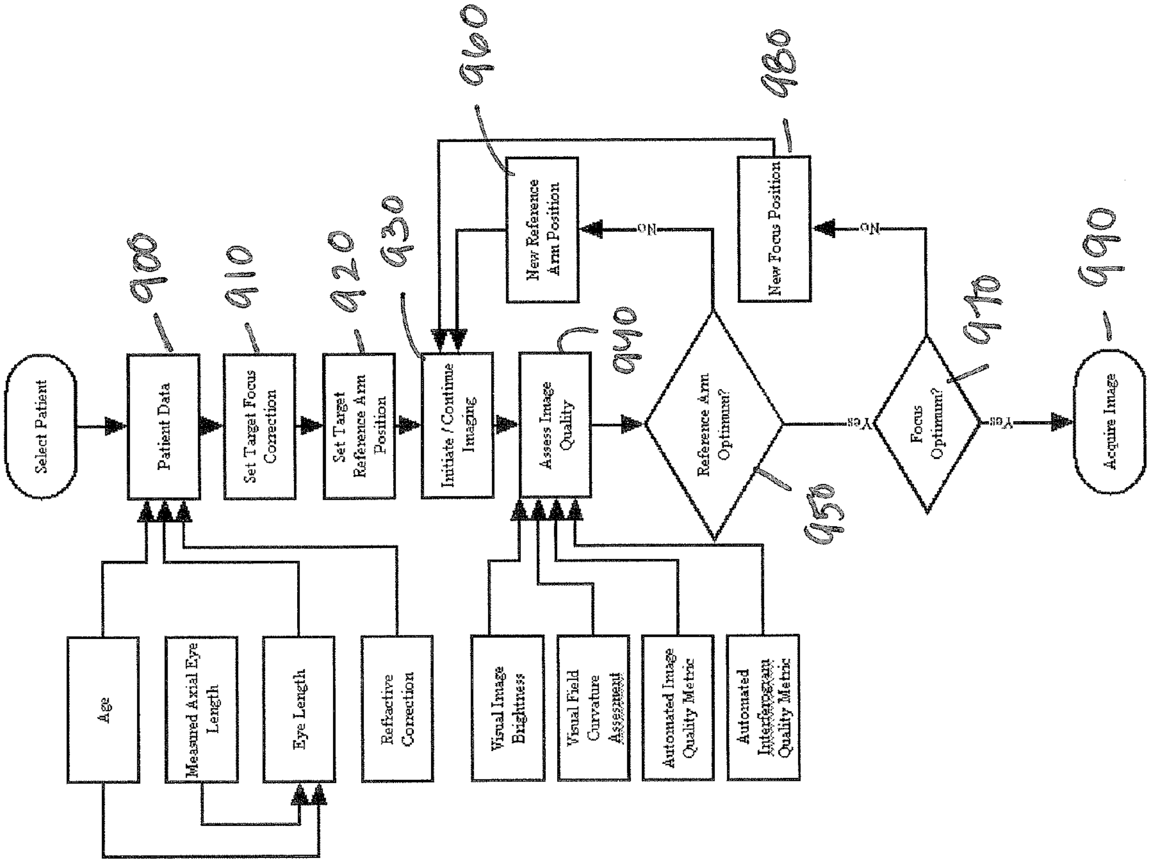
FIG. 8 is a flowchart illustrating focus and reference optimization operations in accordance with some embodiments of the present invention.

FIG. 8 is a flowchart illustrating focus and reference optimization operations in accordance with some embodiments of the present invention. Operations begin at block 900 by obtaining patient data, such as age of the patient, measure axial eye length of the patient, eye length based on chart for eye growth, refractive correction information and the like. Once the patient data is complete (block 900), a target focus correction and a target reference arm position as discussed above with respect to FIG. 1 are set (blocks 910 and 920). Once the focus correction and reference arm position are set, imaging of the subject may commence (block 930). Once the image is obtained and displayed to the image acquisition technician, the image may be assessed for quality (block 940). The image may be assessed for qualities such as visual image brightness, visual field curvature, automated image quality metric, automated interferogram quality metric and the like. Based on the image quality assessment (block 940), it is determined if the reference arm position is optimum (block 950 If it is determined that the reference arm position is not optimum (block 950), the reference arm position may be adjusted (block 960) and a new image may be acquired using the adjusted reference arm position (block 930). Once the reference arm position is correct the focus may be optimized. Similarly, based on the image quality assessment (block 940), it is determined if the focus correction is optimum (block 970). If it is determined that the focus correction is not optimum (block 970), the focus position may be adjusted (block 980) and a new image may be acquired using the adjusted focus position (block 930).

If it is determined that both the reference arm position and the focus position are optimum (blocks 950 and 970), the image may be acquired using the fully adjusted OCT system in accordance with some embodiments of the present invention (block 990). Acquisition of the image (block 990) may include display of the image on an electronic display associated with the OCT system.

Although embodiments of the present invention discussed with respect to FIG. 8 discuss adjustment of the reference arm position first and then adjustment of the focus position, embodiments of the present invention are not limited to this configuration. For example, the steps could be reversed or performed simultaneously without departing from the scope of the present invention.

Figure 10:
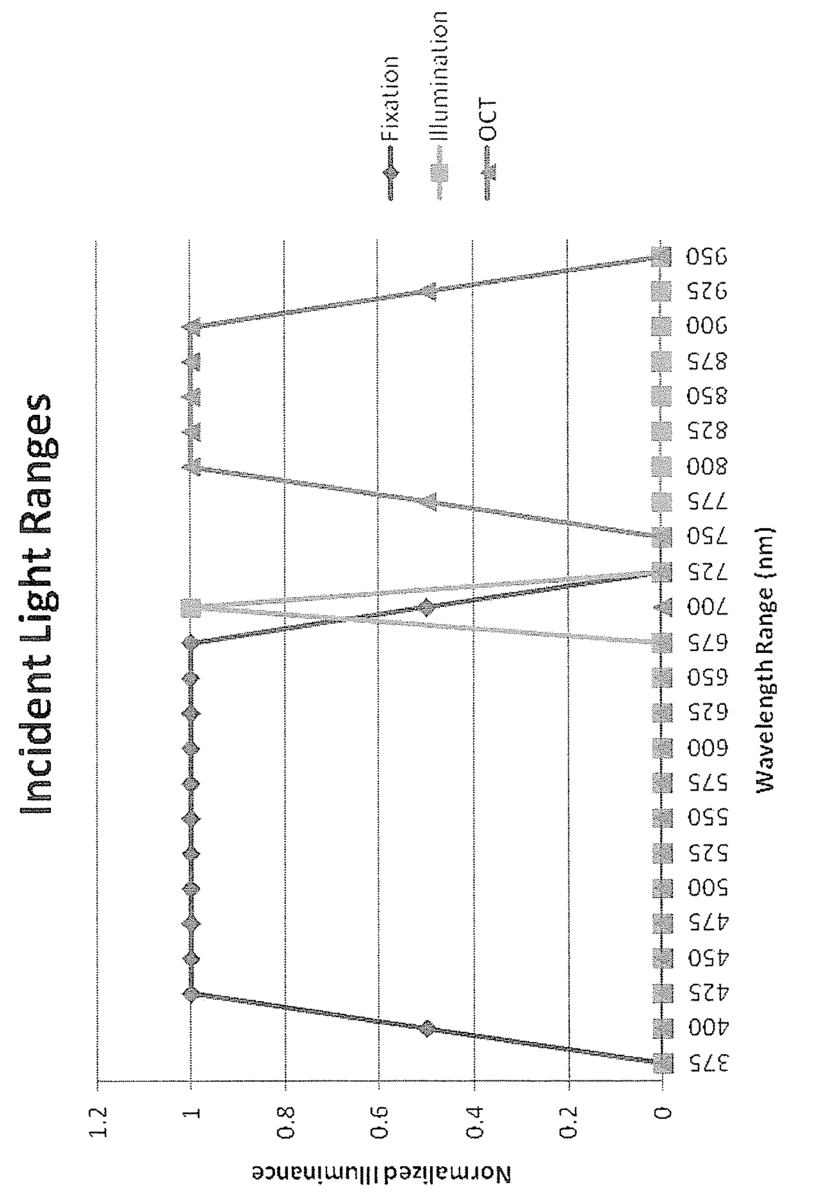
FIG. 10 is a graph of normalized illuminance vs. wavelength illustrating wavelength allocation of optical path lengths scan head in accordance with some embodiments of the present invention.
Figure 11:
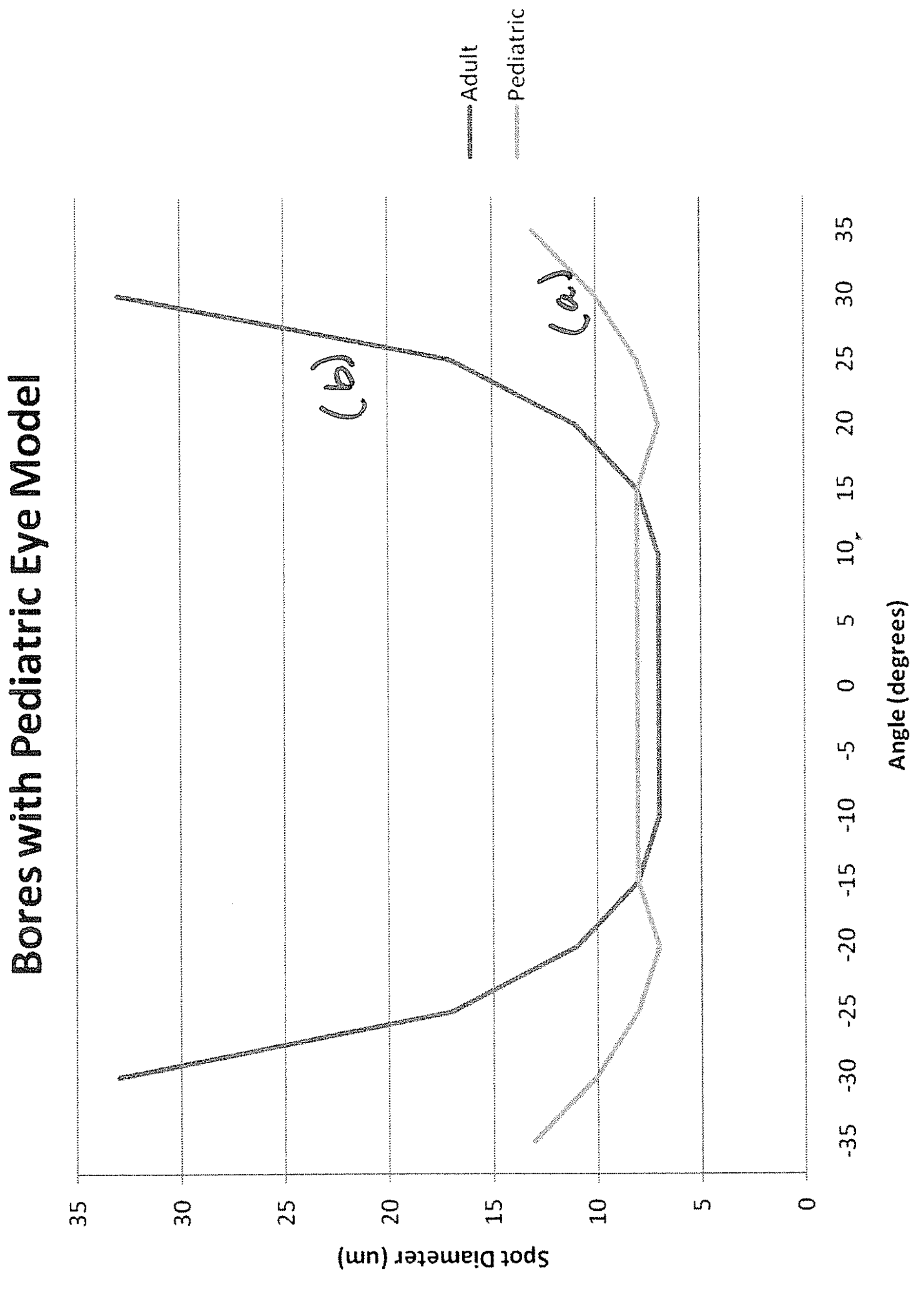
FIG. 11 is a graph of spot diameter vs. angle illustrating field of view defined by lateral resolution imaging pediatric eye with different optics in accordance with some embodiments of the present invention.

FIG. 10 is a graph of normalized illuminance vs. wavelength illustrating wavelength allocation of optical path lengths scan head in accordance with some embodiments of the present invention. FIG. 11 is a graph of spot diameter vs. angle illustrating Field of view by lateral resolution imaging pediatric eye with different optics in accordance with some embodiments of the present invention. The (a) curve of FIG. 11 illustrates results using pediatric optimized optics and the (b) curve illustrates results using adult-optimized optics.

Figure 12:
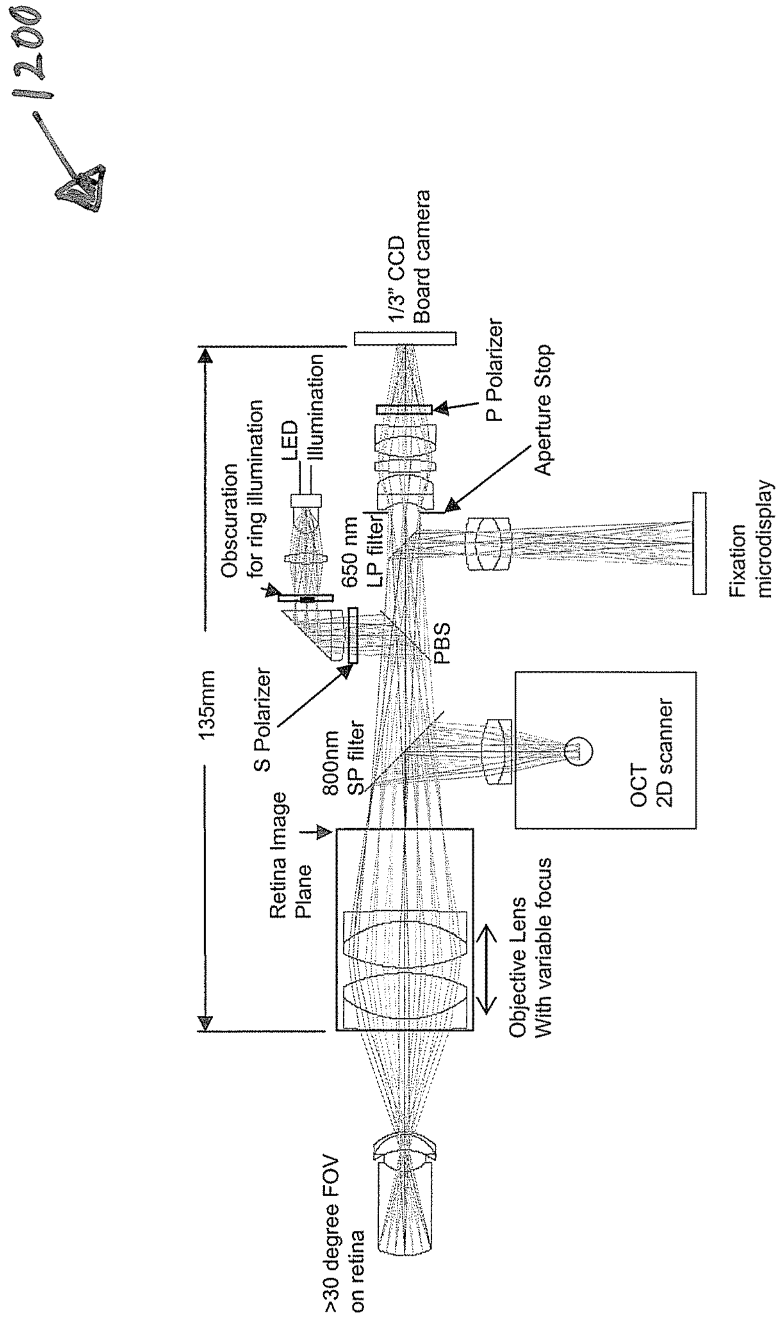
FIG. 12 is a block diagram illustrating a multi-function scanner system including OCT, video or digital fundus image capture, fundus illumination, and discrete or variable fixation target in accordance with some embodiments of the present invention.

FIG. 12 is a block diagram illustrating a multi-function scanner system including OCT, video or digital fundus image capture, fundus illumination, and discrete or variable fixation target in accordance with some embodiments of the present invention. In some embodiments, FIG. 12 illustrates a portable OCT system in accordance with some embodiments of the present invention.

As illustrated in FIG. 12, an exemplary SDOCT system 1200 designed for pediatric and other non-standard patients is illustrated. The optical of the system 1200 of FIG. 12 combines the three primary functions of SDOCT scanning, video fundus illumination and imaging, and a video fixation target-all at a size smaller than currently available handheld slitlamp and fundus camera implementations. The front objective lens forms an image of the retina and then the image is relayed into four paths via beamsplitters. The objective lens has a variable focus and in some embodiments a manual translation capability to accommodate a −12 D to +50 D diopter range of patient spherical error. The working distance to the subject eye is 20 mm.

The OCT path includes a short pass filter configured to reflect wavelengths from 820 nm to 950 nm and transmit wavelengths below 800 nm for the fixation and fundus paths. The OCT path uses a 3 mm diameter fiber collimator incident on the 2D scanner, with a lens to form an image or the fiber at the retina image plane. The combined focal lengths of the objective and OCT lens are designed to deliver a 2 mm diameter collimated beam on the cornea. This may yield a 16 um diameter Gaussian spot on the retina. The pivot point of the scanner and the pupil on the eye are conjugate points. Thus, scanning through the amydriatic eye may be possible.

The fundus imaging and illumination path provide video-rate fundus imaging simultaneously with SDOCT imaging may be used as an aid to real-time alignment of the SDOCT probe. A 700 nm LED may be used for illumination providing patient comfort and to provide a clear view of the color microdisplay used for fixation. In some embodiments, the CCD to be used will be an NIR enhanced Sony ⅓" CCD. The technique used for reducing and possibly eliminating glare may use cross polarization with a polarization beamsplitter (PBS) to co-align the illumination and imaging paths. Ring illumination may reduce glare from the cornea.

Figure 14:
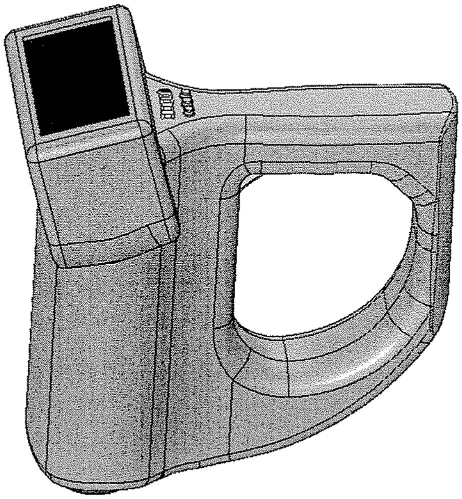
FIG. 14 is a diagram illustrating a mechanical concept for the portable OCT system in accordance with some embodiments of the present invention.

As further discussed above, some embodiments of the present invention provided a good-quality video/digital fundus camera. Mechanical considerations such as the weight, shape and balance of the scanner, as well as ergonomic considerations such as how the operator views the resulting images while manipulating the scanner are variables that can produce success. An exemplary mechanical concept for the case and operator interface design of the handheld scanner is illustrated in FIG. 14. This design includes a case designed to be steadied by being held in both hands, with a rotational Diopter adjustment on the barrel. The novel ergonomic features of the design include a miniature landscape video display for side-by-side simultaneous observation of video fundus and SDOCT images, as well as buttons and controls embedded into the casing to allow for control of SDOCT data acquisition fully independent of the computer keyboard. It will be understood that FIG. 14 is provided for exemplary purposes only and, therefore, embodiments of the present invention are not limited to this configuration.

Figure 15:
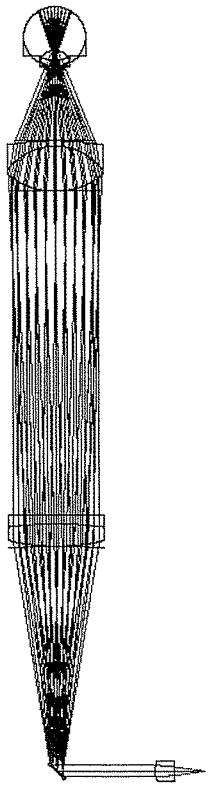
FIG. 15 is a ZEMAX rendering of an optical design for a portable OCT system in accordance with some embodiments of the present invention.
Figure 16:
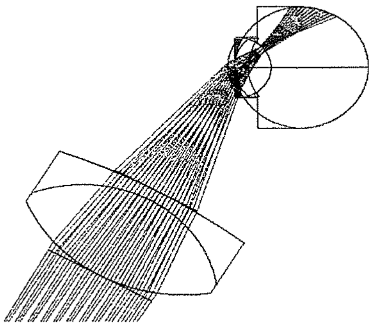
FIG. 16 is ZEMAX diagram illustrating how the design of the portable OCT system allows viewing of the most peripheral retina in accordance with some embodiments of the present invention.

As discussed above, some embodiments of the present invention provide a handheld SDOCT device for pediatric imaging configured with high-speed OCT scanning optics (with expanded FOV and 'iris camera' performance for ease of use) suitable for 2D and 3D retinal imaging as illustrated in FIG. 15. FIG. 15 illustrates a ZEMAX rendering of an exemplary optical design to provide greatly increased FOV, for example, 66° With diffraction limited spot size≦10 um. This design utilizes smaller diameter lenses to allow much closer approach to the eye past the nose, orbital rim, etc as illustrated in FIG. 16. Working distance may be about 20 mm in some embodiments.

FIG. 16 is a ZEMAX illustration of how the system in accordance with some embodiments of the present invention with smaller lenses allows viewing the most peripheral retina (with spot radius≦13 um) by allowing very oblique approach (to 60° from the temporal and inferior directions, and about 45° from the nasal and superior directions as shown in the schematic eye of a newborn.

Figure 17:
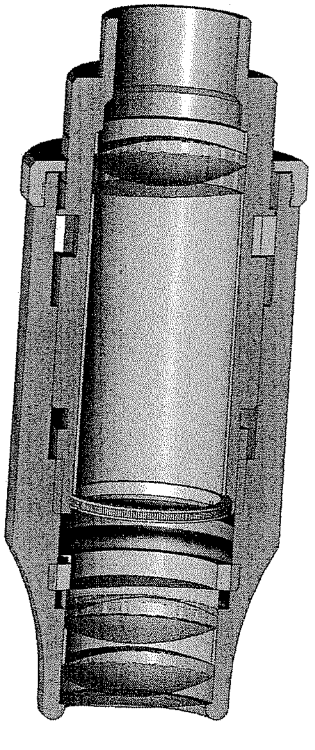
FIG. 17 is a solidworks illustration of a design for the portable OCT optics barrel in accordance with some embodiments of the present invention.
Figure 18:
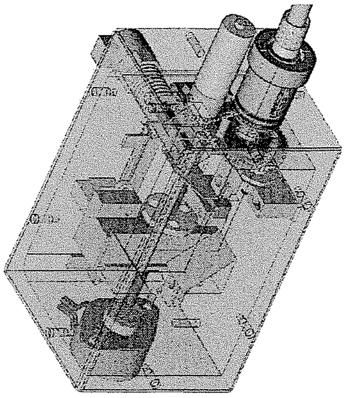
FIG. 18 is a solidworks illustration of a reference arm design with axes for motorized control to translate a retroreflector in accordance with some embodiments of the present invention.

In some embodiments of the present invention, a diopter-calibrated manual twist focus control capable of −12 D to +50 D adjustment is provided on the system as illustrated in FIG. 17. In particular, FIG. 17 is a Solidworks illustration of a design for the portable OCT systems optics barrel, with calibrated manual twist focus control capable of −12 D to +50 D adjustment to allow users to obtain good focus on the retina for 99%+ of the pediatric and general population. FIG. 18 is a Solidworks illustration of a reference arm design with axes for motorized control to translate a retroreflector (corner cube), allowing rapid access to a range of OPLs sufficient to accept 99% of the pediatric and general population.

As discussed above, the initial set point for the reference arm length for patients who eye length (AL) has not been measured, will be set according to an estimate of AL based on patient age (in pediatric patients) and refractive state (if known). Furthermore, in addition to pre-setting the reference arm length to match the expected AL of the patient based on prior A-scan measurement or correlation with patient age and SER, an automatic reference arm tracking of retinal position may also be included in some embodiments of the present invention. Retinal tracking may be implemented using a new compact, motorized reference arm design illustrated in FIG. 18 and control software. This new reference arm design may be adjustable over 200 mm of axial motion, well in excess of the variation in AL expected among the pediatric population and with enough extra length to permit tracking 50 mm of patient/operator relative motion. In some embodiments, the reference arm is driven by a computer-controlled stepper motor which can translate the delay up to 110 mm/sec, which is sufficient to follow operator manipulations of the probe and most patient/operator relative motions. The reference arm position may be controlled by a simple and fast image processing algorithm which will search a subset of SDOCT image A-scans spread across the lateral scan dimension for the prominent ILM reflection, and use this reflection to maintain the reference arm at a position which places the retinal OCT image at the optimal SNR position within the image frame. The ILM reflection can be readily identified on retinal OCT A-scans by a simple threshold algorithm. To keep the algorithm from locking onto other ocular structures (such as the cornea and lens capsule as the probe is advanced), the operator will turn on retinal tracking using a foot pedal switch only after the macular reflection has been obtained. There is no risk to either patient or operator from this control mechanism, which is contained within the engine chassis.

As discussed above, some aspects of the present invention may be implemented by a data processing system. Exemplary embodiments of a data processing system 130 configured in accordance with embodiments of the present invention will be discussed with respect to FIG. 19. The data processing system 1930 may include a user interface 1944, including, for example, input device(s) such as a keyboard or keypad, a display, a speaker and/or microphone, and a memory 1936 that communicate with a processor 1938. The data processing system 1930 may further include I/O data port(s) 1946 that also communicates with the processor 1938. The I/O data ports 1946 can be used to transfer information between the data processing system 1930 and another computer system or a network using, for example, an Internet Protocol (IP) connection. These components may be conventional components such as those used in many conventional data processing systems, which may be configured to operate as described herein.

Figure 19:
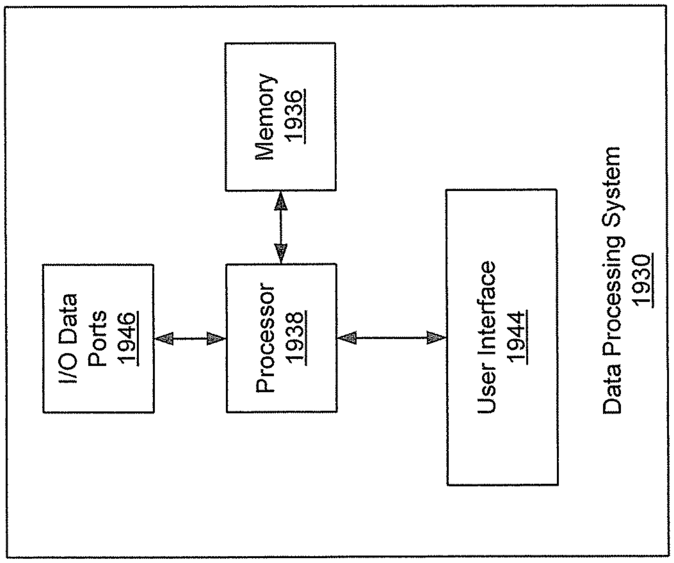
FIG. 19 is a block diagram of a data processing system suitable for use in some embodiments of the present invention.
Figure 20:
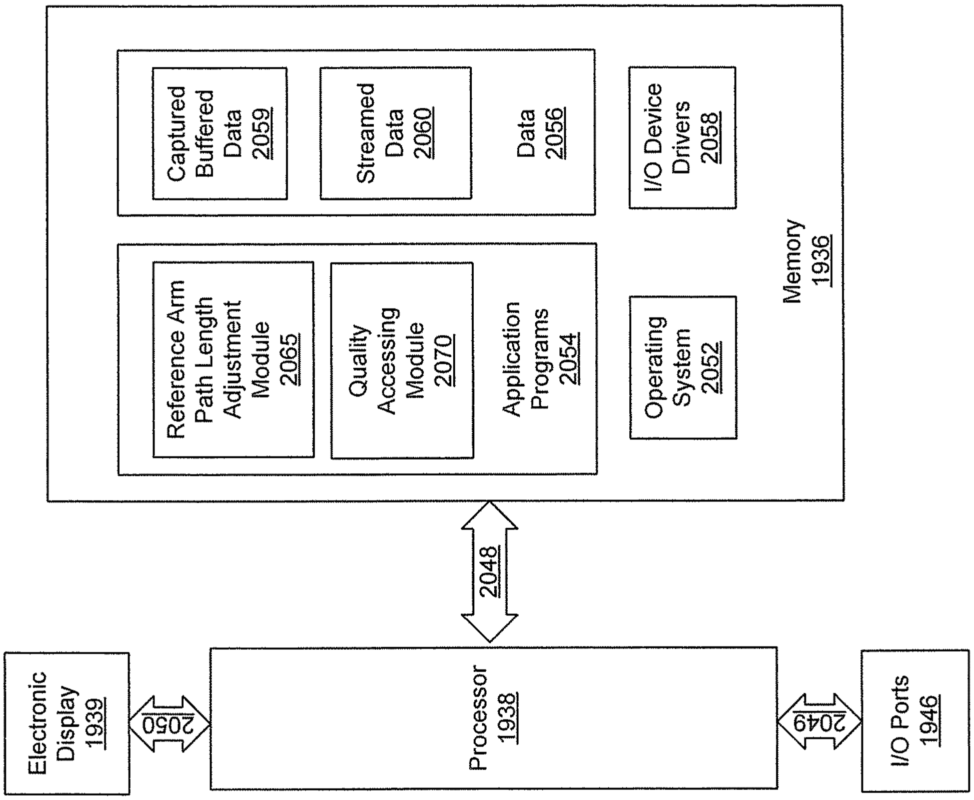
FIG. 20 is a more detailed block diagram of a system according to some embodiments of the present invention.
Figure 1:
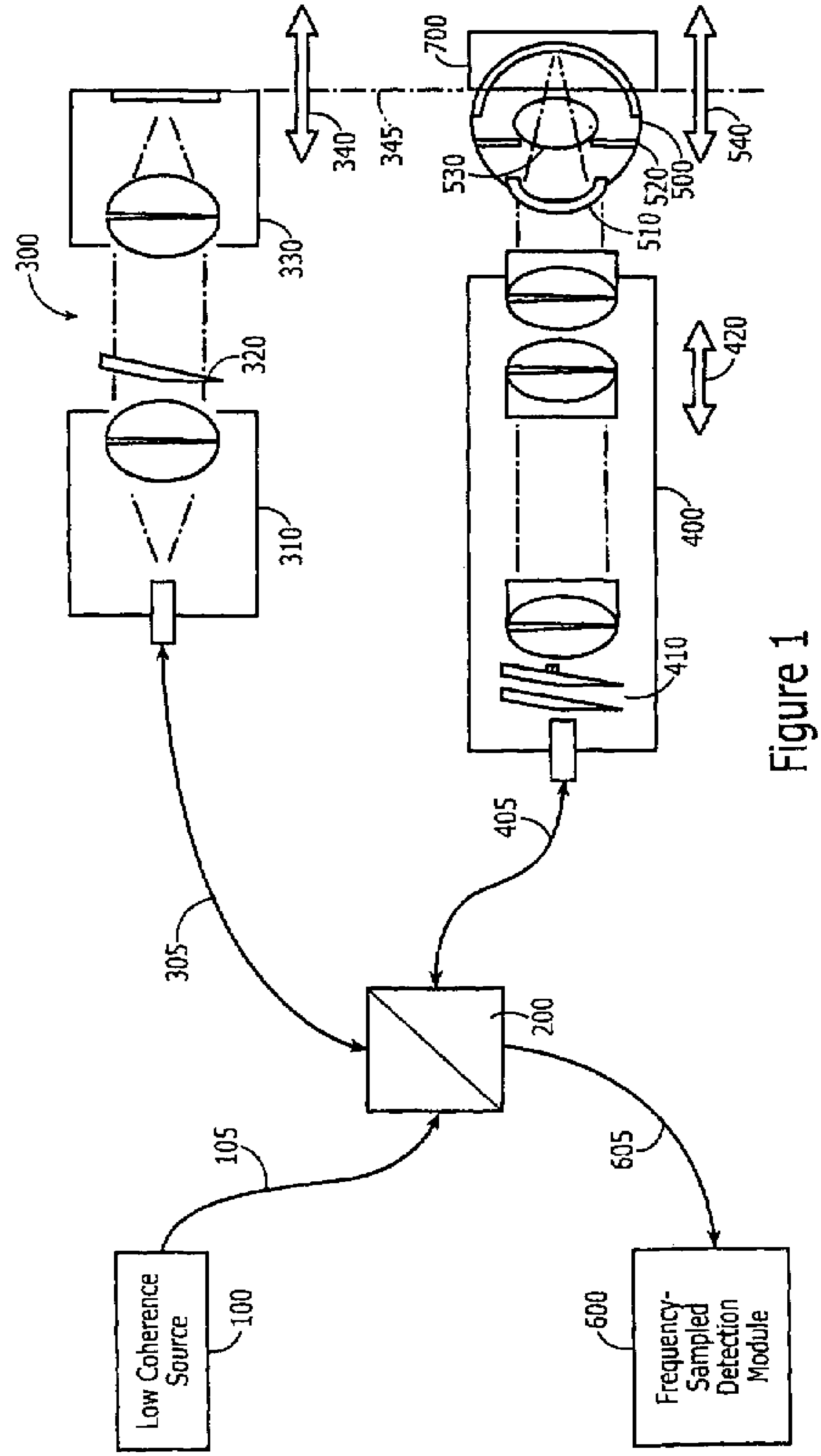
Figure 2:
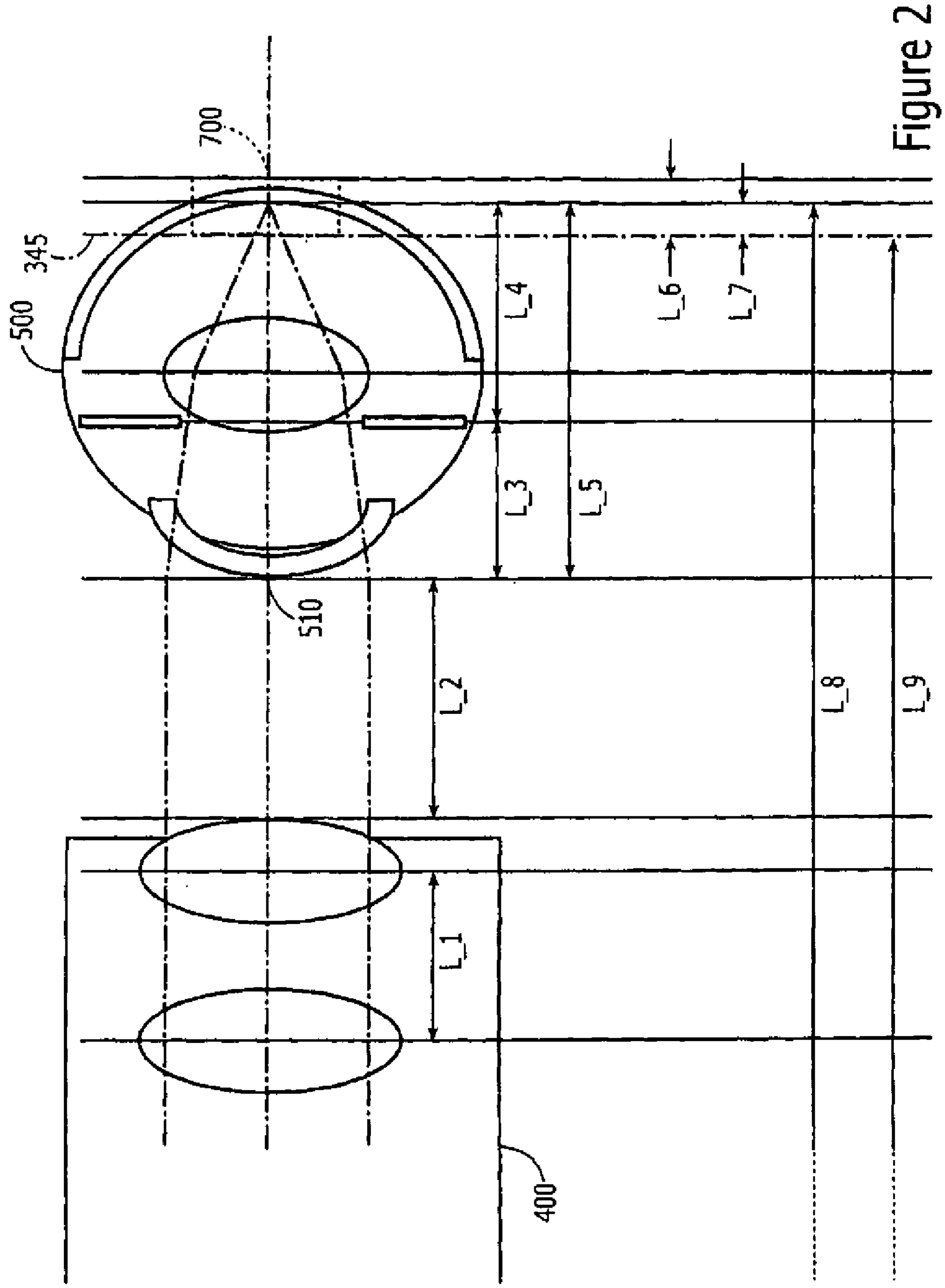
Figure 3:
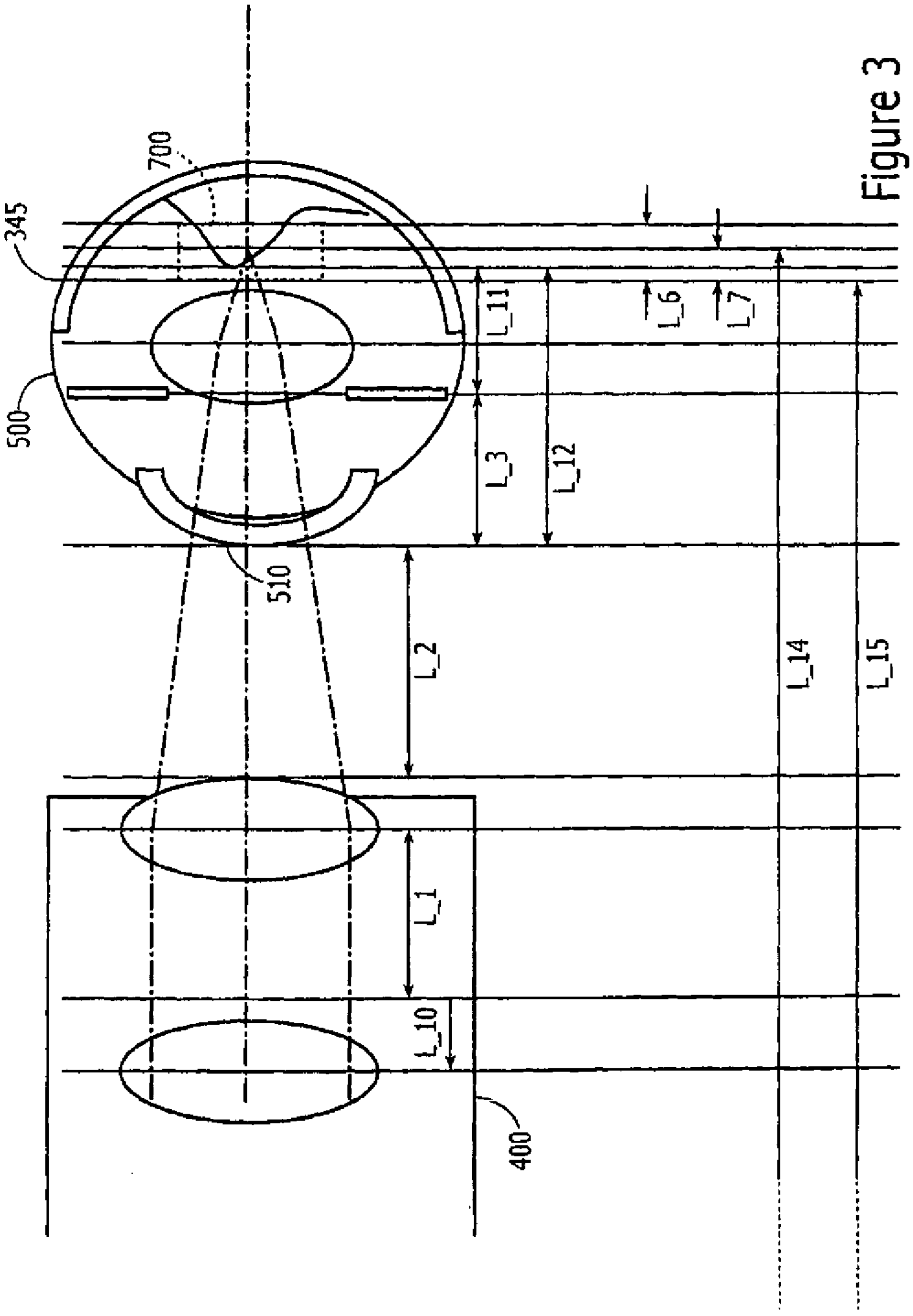
Figure 4:
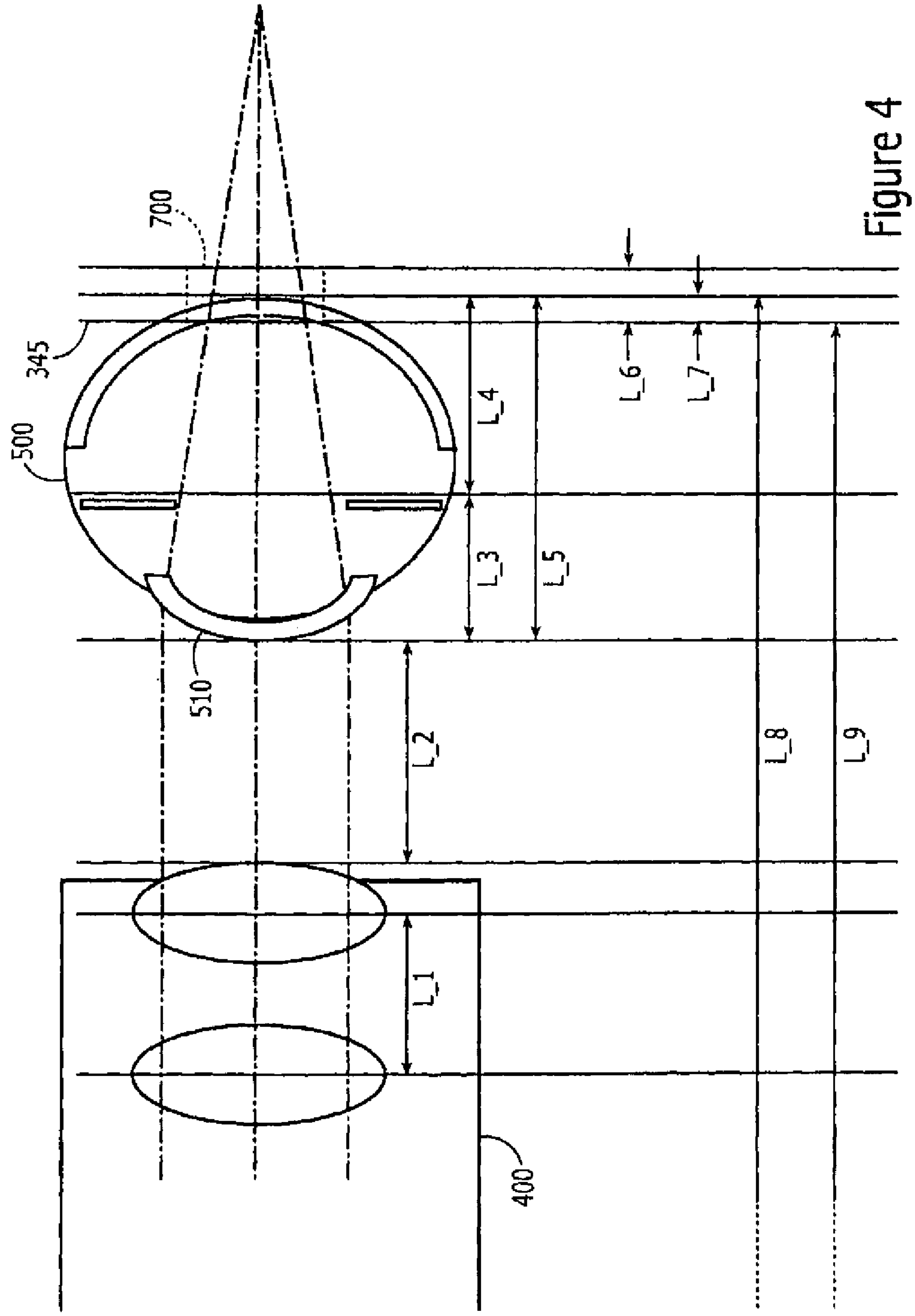
Figure 5:
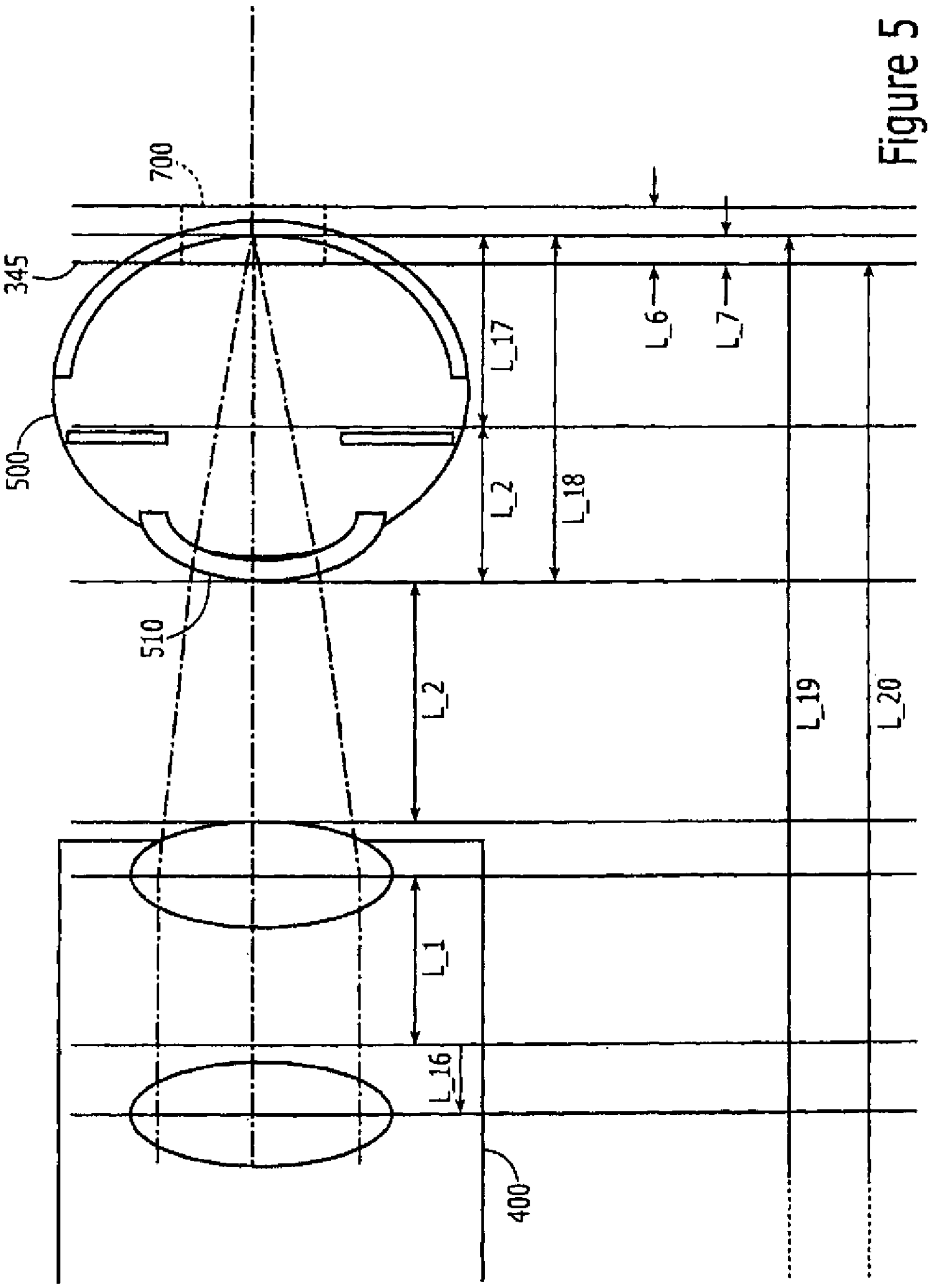
Figure 6:
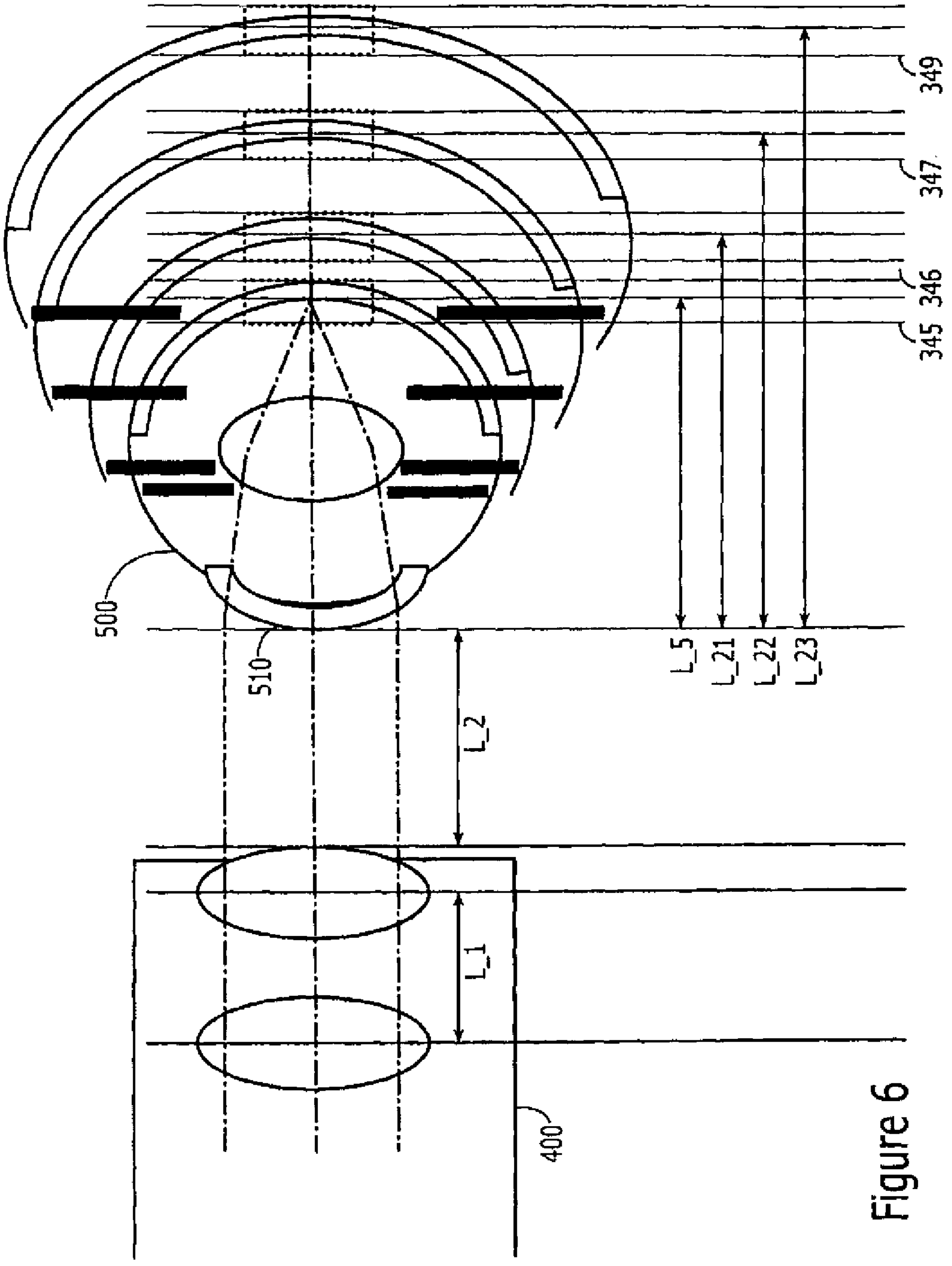

Referring now to FIG. 20, a more detailed block diagram of a data processing system of FIG. 19 is provided that illustrates systems, methods, and computer program products in accordance with some embodiments of the present invention will now be discussed. As illustrated in FIG. 20, the processor 1938 communicates with the memory 1936 via an address/data bus 2048, the I/O data ports 1946 via address/data bus 2049 and the electronic display 1939 via address/data bus 2050. The processor 1938 can be any commercially available or custom enterprise, application, personal, pervasive and/or embedded microprocessor, microcontroller, digital signal processor or the like. The memory 1936 may include any memory device containing the software and data used to implement the functionality of the data processing system 1930. The memory 1936 can include, but is not limited to, the following types of devices: ROM, PROM, EPROM, EEPROM, flash memory, SRAM, and DRAM.

As further illustrated in FIG. 20, the memory 136 may include several categories of software and data used in the system: an operating system 2052; application programs 2054; input/output (I/O) device drivers 2058; and data 2056. As will be appreciated by those of skill in the art, the operating system 2052 may be any operating system suitable for use with a data processing system, such as OS/2, AIX or zOS from International Business Machines Corporation, Armonk, N.Y., Windows95, Windows98, Windows2000 or WindowsXP, or Windows CE from Microsoft Corporation, Redmond, Wash., Palm OS, Symbian OS, Cisco IOS, VxWorks, Unix or Linux. The I/O device drivers 2058 typically include software routines assessed through the operating system 2052 by the application programs 2054 to communicate with devices such as the I/O data port(s) 1946 and certain memory 1936 components. The application programs 2054 are illustrative of the programs that implement the various features of the some embodiments of the present invention and may include at least one application that supports operations according to embodiments of the present invention. Finally, as illustrated, the data 2056 may include captured buffer data 2059 and streamed data 260, which may represent the static and dynamic data used by the application programs 2054, the operating system 2052, the I/O device drivers 2058, and other software programs that may reside in the memory 1036.

As further illustrated in FIG. 20, according to some embodiments of the present invention, the application programs 2054 include a reference arm path length adjustment module 2065 and a quality assessing module 2070. While the present invention is illustrated with reference to the reference arm path length adjustment module 2065 and the quality assessing module 2070 as being application programs in FIG. 20, as will be appreciated by those of skill in the art, other configurations fall within the scope of the present invention. For example, rather than being application programs 2054, these circuits and modules may also be incorporated into the operating system 2052 or other such logical division of the data processing system. Furthermore, while the reference arm path length adjustment module 2065 and the quality assessing module 2070 are illustrated in a single system, as will be appreciated by those of skill in the art, such functionality may be distributed across one or more systems. Thus, the present invention should not be construed as limited to the configuration illustrated in FIG. 20, but may be provided by other arrangements and/or divisions of functions between data processing systems. For example, although FIG. 20 is illustrated as having various circuits, one or more of these circuits may be combined without departing from the scope of the present invention.

Details of operations of the reference arm path length adjustment module 2065 are discussed above. The quality assessing module 2070 is configured to aid a technician in assessing the quality of an image creating using systems in accordance with some embodiments of the present invention. In some embodiments, the quality assessing module may be configured to display an acquired image to an image acquisition technician; trigger adjustment of the reference arm path length and/or focusing of at least one lens in the sample arm based on an assessed quality of the displayed image; and trigger the OCT system to initiate or continue acquisition of the image after adjustments are made.

Some embodiments of the present invention provide optical coherence tomography (OCT) imaging systems for imaging an eye including a source having an associated source arm path and a reference arm having an associated reference arm path coupled to the source path, the reference arm path having an associated reference arm path length. A sample having an associated sample arm path coupled to the source arm and a detector path having a detector are provided. The sample path and the reference path couple to the detector path to provide an interferometric optical signal to the detector. A reference arm path length adjustment module is coupled to the reference arm. The reference arm path length adjustment module is configured to adjust the reference arm path length such that the reference arm path length is matched to the sample arm path length that includes an eye length of the subject.

In further embodiments of the present invention, the OCT imaging system is a Fourier domain optical coherence tomography (FD-OCT) imaging system. The FD-OCT imaging system may be a Spectral-domain OCT (SD-OCT) imaging system. SD-OCT uses a broadband light source and achieves spectral discrimination with a dispersive spectrometer in the detector arm. Alternatively, the FD-OCT imaging system may be a swept-source OCT (SS-OCT) imaging system. SS-OCT time-encodes wavenumber by rapidly tuning a narrowband source through a broad optical bandwidth. The FD-OCT imaging system may utilize aspects of both SD-OCT and SS-OCT. In further embodiments of the present invention, the reference arm path length may be adjusted to accommodate eye lengths ranging from about 10 mm to about 30 mm, and preferable to accommodate eye lengths ranging from about 2 mm to about 50 mm, to accommodate fetal development and the mature eye of larger animal models. The reference arm optical path length may be optimized to correspond with a prescribed range of offsets to a sample arm optical path length as measured to a focal plane of the OCT system. The reference arm path length may generally be selected to be offset from the sample arm path length as measured to a focal plane of the OCT imaging system with a range of 0 mm to 2 mm, and may be less than or greater than the corresponding sample arm path length.

In still further embodiments of the present invention, at least one lens of the OCT system is provided in the sample arm path and at least one refracting surface of the subject eye is provided in the sample arm path, the at least one lens and at least one refracting surface of the subject eye defining an optical system having an optical field curvature that matches a physical curvature of a retina of the eye of the subject. The at least one lens may be configured to image a mature eye or an immature eye. A distance from a cornea to a retina of the mature eye may be about 25 mm and a the distance from the cornea to the retina of the pediatric eye may be from about 14 mm to about 25 mm.

In some embodiments of the present invention, the at least one lens may have an associated focus adjustment that enables imaging into both anterior and posterior portions of the eye of the subject.

In some embodiments of the present invention, the at least one lens may have an associated focus adjustment that enables imaging into anterior regions of the posterior chamber of the eye of the subject.

In further embodiments of the present invention, the system may be a wide field imaging system providing a field of view of about 50 degrees.

In still further embodiments of the present invention, the reference arm path length adjustment module may be configured to set a target reference arm path length based on an age of the subject; a refractive status of the eye of the subject; and/or adjust the target reference arm path length based on additional information pertaining to the subject. The additional information pertaining to the subject may include measured axial eye length of the subject and/or any relevant test results.

In some embodiments of the present invention, the OCT system may be portable such that the OCT the system is provided to the subject where the subject is located. The portable OCT system may be configured to be moved to a location of the subject, unplugged and/or receive new samples without being shutdown.

In some embodiments of the present invention, the OCT system may be portable such that the OCT the system is provided to the subject in any orientation of the subject. The portable OCT system may be aligned to the subject whether the subject is sitting, standing, lying prone, lying supine, at any associated angle.

In further embodiments of the present invention, the portable OCT system may include a portable handheld OCT probe; a battery backup device associated with the portable handheld probe; and a moveable rack configured to receive the portable handheld probe and/or the battery backup device.

In still further embodiments of the present invention, the portable OCT system may further include a fixation target for the subject configured to provide a comfort image to the subject during image acquisition. The fixation target may be configured to provide a continuously variable patient comfort image. The fixation target may include an image of a character, a photograph, or an icon, and the image photograph or icon may be animated to maintain the subject's attention and relaxation.

In some embodiments of the present invention, the portable OCT system may be configured to provide a visible light that reflects off a cornea of the eye of the subject to enable accurate positioning of the portable OCT system.

In further embodiments of the present invention, the portable OCT system may include a video and/or digital fundus camera. The video and/or digital fundus camera may be aligned and calibrated to the OCT system.

In still further embodiments of the present invention, the portable OCT system may further include a foot peddle and/or finger trigger configured to control focus adjustment, reference arm path length adjustment and/or trigger acquisition of an image.

In still further embodiments of the present invention, the portable OCT system may further include a foot peddle and/or finger trigger configured to control the OCT source power, attenuation of OCT signal power in the reference arm path, the power of the illumination for the video or digital fundus camera.

In some embodiments of the present invention, the portable OCT system may be configured to provide two synchronous images to illustrate orthogonal pathology of an eye of the subject to facilitate aiming of the portable OCT system during image acquisition.

In further embodiments of the present invention, the portable OCT system may be configured to continuously acquire, process and display images until detection of an image capture trigger signal; and record a predetermined buffered portion of the acquired image upon detection of the image capture trigger signal. In certain embodiments, the buffered image comprises the most recent from about 2.0 seconds to about 30 seconds of the acquired image.

In still further embodiments of the present invention, the continuously acquired image may be streamed non-volatile storage for a predetermined period of time.

In some embodiments of the present invention, the system includes a quality-assessing module configured to figure of merit for the quality of an acquired image; trigger adjustment of the reference arm path length and or focusing of at least one lens in the sample arm based on an assessed quality of the displayed image; and trigger the OCT system to initiate or continue acquisition of the image after adjustments are made.

In further embodiments of the present invention the OCT system may be configured to acquire an image from an aphakic subject that does not have an ocular lens in the eye being imaged.

In further embodiments of the present invention the OCT system may be configured to acquire an image of pathologies that are substantially anterior to the posterior pole, or retina of the subject, but still nominally within the anterior chamber of the eye of the subject. In still further embodiments of the present invention, the OCT system may be a pediatric OCT system.

Some embodiments of the present invention provide OCT imaging systems for imaging an eye including a source having an associated source arm path and a reference arm having an associated reference arm path coupled to the source path, the reference arm path having an associated reference arm path length. A sample having an associated sample arm path coupled to the source arm and reference arm paths is provided. At least one lens is provided in the sample arm path, the at least one lens having a field curvature that matches a curvature of a retina of the eye of the subject.

Further embodiments of the present invention provide methods for imaging an eye in an optical coherence tomography (OCT) imaging system including setting a target reference arm path length of the OCT system such that the reference arm path length is matched to an eye length of a subject; obtaining additional information about the subject relevant to the target reference arm path length; recalibrating the reference arm path length based on the obtained information; and adjusting the reference arm path length based on the recalibrated reference arm path length.

In still further embodiments of the present invention, an image is acquired using the OCT system having the adjusted reference arm path length. The method may further include accessing the image quality of the acquired image; determining if the adjusted reference arm path length is optimum; further adjusting the reference arm path length if it is determined that the adjusted reference arm path length is not optimum; and reacquiring the image using the OCT system having the further adjusted reference arm path length.

In still further embodiments of the present invention adjusting the reference arm path length is accomplished manually or automatically based on feedback from an operator or an image quality metric on an acquired image.

In still further embodiments of the present invention the quality metric is the average or peak brightness of the image.

In some embodiments of the present invention, the steps of accessing, determining, further adjusting and reacquiring may be repeated until an image having a desired quality is obtained.

In further embodiments of the present invention, further adjusting is followed by determining if a focus of at least one objective lens of the OCT system is optimum; and adjusting focus position of the at least one objective lens of the OCT system if it is determined that the focus of the at least one objective lens is not optimum, wherein reacquiring the image further comprises reacquiring the image using the OCT system having the further adjusted reference arm path length and the adjusted focus.

In still further embodiments of the present invention adjusting the focus is accomplished manually or automatically based on feedback from an operator or an image quality metric on an acquired image.

In still further embodiments of the present invention the quality metric is the average or peak brightness of the image.

Still further embodiments of the present invention provide computer program products for imaging an eye in OCT imaging systems including computer readable storage medium having computer readable program code embodied in said medium. The computer readable program code includes computer readable program code configured to set a target reference arm path length of the OCT system such that the reference arm path length is matched to an eye length of a subject; computer readable program code configured to obtain additional information about the subject relevant to the target reference arm path length; computer readable program code configured to recalibrate the reference arm path length based on the obtained information; computer readable program code configured to automatically adjust the reference arm path length based on the recalibrated reference arm path length; and computer readable program code configured to acquire an image using the OCT system having the adjusted reference arm path length and display the acquired image on an electronic display associated with the OCT system.

Example embodiments are described above with reference to block diagrams and/or flowchart illustrations of methods, devices, systems and/or computer program products. It is understood that a block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means (functionality) and/or structure for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the functions/acts specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, example embodiments may be implemented in hardware and/or in software (including firmware, resident software, micro-code, etc.). Furthermore, example embodiments may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random assess memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Computer program code for carrying out operations of data processing systems discussed herein may be written in a high-level programming language, such as Java, AJAX (Asynchronous JavaScript), C, and/or C++, for development convenience. In addition, computer program code for carrying out operations of example embodiments may also be written in other programming languages, such as, but not limited to, interpreted languages. Some modules or routines may be written in assembly language or even micro-code to enhance performance and/or memory usage. However, embodiments are not limited to a particular programming language. It will be further appreciated that the functionality of any or all of the program modules may also be implemented using discrete hardware components, one or more application specific integrated circuits (ASICs), or a programmed digital signal processor or microcontroller.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated.

In the drawings and specification, there have been disclosed exemplary embodiments of the invention. However, many variations and modifications can be made to these embodiments without substantially departing from the principles of the present invention. Accordingly, although specific terms are used, they are used in a generic and descriptive sense only and not for purposes of limitation, the scope of the invention being defined by the following claims.

That which is claimed is:

1. An optical coherence tomography (OCT) imaging system for imaging an eye, the system comprising:
- a source having an associated source arm path;
- a reference arm having an associated reference arm path coupled to the source path, the reference arm path having an associated reference arm path length;
- a sample arm having an associated sample arm path coupled to the source arm, the sample arm comprising at least one lens, wherein the at least one lens has an associated focus adjustment configured to enable imaging a retina in one focal setting and to enable imaging a structure anterior to the retina within the posterior chamber in a second focal setting; and
- a reference arm path length adjustment module coupled to the reference arm,
- wherein a range of the reference arm adjustment is at least 15 mm;
- wherein 15 mm defines a optical path length difference between and eye length of a premature infant eye and an eye length of an adult eye; and
- wherein the reference arm path length is adjusted coarsely to accommodate an eye length and finely to adjust to a prescribed offset between a reference position and a focal plane within the sample of the at least one lens.

2. The OCT system of claim 1, wherein the reference arm path length is adjusted to accommodate subject eye lengths in the sample arm ranging from about 2.0 mm to about 50 mm.

3. The OCT system of claim 1, further comprising a lens system comprising at least one lens in the sample arm path and at least one surface of the eye, the lens system having a field curvature that matches a curvature of a retina of the eye of the subject.

4. The OCT system of claim 3, wherein the at least one lens is configured to image a mature eye or a pediatric eye.

5. The OCT system of claim 4, wherein a distance from a cornea to a retina of the mature eye is about 25 mm and a the distance from the cornea to the retina of the pediatric eye is from about 14 mm to about 25 mm.

6. The OCT system of claim 3, wherein the at least one lens has an associated focus adjustment that enables imaging into both anterior and posterior regions of the posterior chamber of the eye of the subject.

7. The OCT system of claim 6, wherein the focus adjustment accommodates at least +30D of additional focal power.

8. The OCT system of claim 6, wherein the focus adjustment accommodates at least +50D of additional focal power.

9. The OCT system of claim 6, wherein the focus adjustment accommodates at up to +100D of additional focal power.

10. The OCT system of claim 1, wherein the system is a wide field imaging system providing a field of view of about equal to or greater than 50 degrees.

11. The OCT system of claim 1, wherein the system is a wide field imaging system providing a field of view of about equal to or greater than 140 degrees in combination with rotation about a pupil.

12. The OCT system of claim 1, wherein the reference arm path length adjustment module is configured to set a reference arm path length based on an age of the subject.

13. The OCT system of claim 12, wherein the reference arm path length adjustment module is configured to set a target reference arm path length based on additional information pertaining to the subject; the additional information comprising:
- a refractive status of the eye of the subject;
- measured axial eye length of the subject; and/or
- any relevant test results.

14. The OCT system of claim 1, wherein the OCT system is portable such that the OCT system is provided to the subject where the subject is located.

15. The OCT system of claim 14, wherein the portable OCT system is configured to provide imaging to a subject independent of the orientation of the subject.

16. The OCT system of claim 14, wherein the portable OCT system is configured to be moved to a location of the subject, unplugged and/or receive new samples without being shutdown.

17. The OCT system of claim 14, wherein the portable OCT system comprises:
- a portable handheld OCT probe;
- a battery backup device associated with the portable handheld probe; and
- a moveable rack configured to receive the portable handheld probe and/or the battery backup device.

18. The OCT system of claim 14, wherein the portable OCT system further comprises a fixation target for the subject configured to provide a comfort image to the subject during image acquisition.

19. The OCT system of claim 14, wherein the fixation target is configured to provide a continuously variable patient comfort image.

20. The OCT system of claim 14, wherein the portable OCT system is configured to provide a visible light that reflects off a cornea of the eye of the subject to enable accurate positioning of the portable OCT system.

21. The OCT system of claim 14, wherein the portable OCT system comprises a video and/or digital fundus camera.

22. The OCT system of claim 14, wherein the portable OCT system further comprises a foot peddle and/or finger trigger configured to control focus adjustment, reference arm path length adjustment and/or trigger acquisition of an image.

23. The OCT system of claim 14, wherein the portable OCT system is configured to provide two orthogonal images to illustrate pathology of an eye of the subject to facilitate aiming of the portable OCT system during image acquisition.

24. The OCT system of claim 14, wherein the portable OCT system configured to:
- continuously acquire images until detection of an image capture trigger is detected; and
- record a predetermined buffered portion of the acquired image upon detection of the image capture trigger.

25. The OCT system of claim 24, wherein the buffered image comprises the most recent from about 2.0 seconds to about 30 seconds of the acquired image.

26. The OCT system of claim 24, wherein the continuously acquired image is streamed to a non-volatile storage for a predetermined period of time.

27. The OCT system of claim 1, further comprising a quality assessing module, the quality assessing module configured to:
- display an acquired image to an image acquisition technician;

trigger adjustment of the reference arm path length and/or focusing of at least one lens in the sample arm based on an assessed quality of the displayed image; and trigger the OCT system to initiate or continue acquisition of the image after adjustments are made.

28. The OCT system of claim 1, wherein the OCT system is configured to acquire an image from an aphakic subject.

29. The OCT system of claim 1, wherein the OCT system comprises a pediatric OCT system.

30. The OCT system of claim 1, wherein the reference arm path length adjustment module is configured to automatically adjust the reference arm path length such that the reference arm path length is based on an eye length of the subject.

31. An optical coherence tomography (OCT) imaging system for imaging an eye, the system comprising:

a source having an associated source arm path;

a reference arm having an associated reference arm path coupled to the source path, the reference arm path having an associated reference arm path length;

a sample arm having an associated sample arm path coupled to the source arm, the sample arm comprising at least one lens, wherein the at least one lens has an associated focus adjustment configured to enable imaging a retina in one focal setting and to enable imaging a structure anterior to the retina within the posterior chamber in a second focal setting; and a reference arm path length adjustment module coupled to the reference arm, wherein a range of the reference arm adjustment is at least 15 mm;

wherein 15 mm defines a optical path length difference between and eye length of a premature infant eye and an eye length of an adult eye;

wherein the reference arm path length is adjusted coarsely to accommodate an eye length and finely to adjust to a prescribed offset between a reference position and a focal plane within the sample of the at least one lens; and wherein the at least one lens has a field curvature based on a curvature of a retina of the eye of the subject.

32. The OCT system of claim 31, wherein the at least one lens is configured to image a mature eye or a pediatric eye.

33. The OCT system of claim 31, wherein the reference arm path length is adjustable up to at least about 11 mm.

34. The OCT system of claim 31, wherein the at least one lens has an associated focus adjustment that enables imaging into both anterior and posterior portions of the eye of the subject.

35. The OCT system of claim 34, wherein the OCT system is portable such that the OCT the system is provided to the subject where the subject is located and at the orientation in which the subject is oriented.

36. A computer program product for imaging an eye in an optical coherence tomography (OCT) imaging system, the computer program product comprising:

a non-transitory, computer readable storage medium having computer readable program code embodied in the medium, the computer readable program code comprising:

computer readable program code configured to set a target reference arm path length of the OCT system such that the reference arm path length is based on an eye length of a subject;

computer readable program code configured to obtain additional information about the subject relevant to the target reference arm path length;

computer readable program code configured to recalibrate the reference arm path length based on the obtained information;

computer readable program code configured to automatically adjust the reference arm path length based on the recalibrated reference arm path length, wherein the computer readable program code configured to automatically adjust comprises computer readable program code configured to adjust the reference arm path length at least 15 mm, wherein 15 mm defines a minimum optical path length difference between an eye length of a premature infant eye and an eye length of an adult eye and wherein the reference arm path length is adjusted coarsely to accommodate an eye length and finely to adjust to a prescribed offset between a reference position and a focal plane within the sample of the at least one lens; and computer readable program code configured to acquire an image using the OCT system having the adjusted reference arm path length and display the acquired image on an electronic display associated with the OCT system.

* * * * *

UNITED STATES PATENT AND TRADEMARK OFFICE

CERTIFICATE OF CORRECTION

PATENT NO. : 8,421,855 B2
APPLICATION NO. : 12/428603
DATED : April 16, 2013
INVENTOR(S) : Buckland et al.

It is certified that error appears in the above-identified patent and that said Letters Patent is hereby corrected as shown below:

Title page should be deleted and substitute therefor the attached title page.

In the Drawings:

Please replace drawings of Figures 1 through 20 with replacement drawings of Figures 1 through 20 as attached.

In the Claims:

Column 22 Claim 19, Line 34:
Please replace "system of claim 14," to read -- system of claim 18, --.

Signed and Sealed this
Twenty-second Day of October, 2013

Teresa Stanek Rea
*Deputy Director of the United States Patent and Trademark Office*

(12) United States Patent
Buckland et al.
(10) Patent No.: US 8,421,855 B2
(45) Date of Patent: Apr. 16, 2013

(54) OPTICAL COHERENCE TOMOGRAPHY (OCT) IMAGING SYSTEMS FOR USE IN PEDIATRIC OPHTHALMIC APPLICATIONS AND RELATED METHODS AND COMPUTER PROGRAM PRODUCTS

(75) Inventors: Eric L. Buckland, Hickory, NC (US); Robert H. Hart, Cary, NC (US); Glenn A. Myers, Durham, NC (US); Joseph A. Izatt, Raleigh, NC (US)

(73) Assignee: Bioptigen, Inc., Durham, NC (US)

( * ) Notice: Subject to any disclaimer, the term of this patent is extended or adjusted under 35 U.S.C. 154(b) by 878 days.

(21) Appl. No.: 12/428,603

(22) Filed: Apr. 23, 2009

(65) Prior Publication Data

US 2009/0268020 A1 Oct. 29, 2009

Related U.S. Application Data

(60) Provisional application No. 61/047,265, filed on Apr. 23, 2008.

(51) Int. Cl.
*A61B 3/10* (2006.01)
*A61B 3/107* (2006.01)
*A61B 5/00* (2006.01)

(52) U.S. Cl.
USPC .......... 348/78; 348/77

(58) Field of Classification Search .......... 348/78, 348/77
See application file for complete search history.

(56) References Cited

U.S. PATENT DOCUMENTS 6,053,613 A 4/2000 Wei et al.
6,741,359 B2 5/2004 Wei et al.
7,140,730 B2 11/2006 Wei et al.
7,784,941 B2 * 8/2010 Fukuma et al. .......... 351/205
8,049,899 B2 * 11/2011 Waelti et al. .......... 356/497
2007/0076217 A1 4/2007 Baker et al.
2007/0159595 A1 * 7/2007 Fukuma et al. .......... 351/206

(Continued)

FOREIGN PATENT DOCUMENTS

EP 1 738 680 A1 1/2007
EP 1 806 092 A1 7/2007
WO WO 2007/065670 A2 6/2007
WO WO 2008/052793 A1 5/2008

OTHER PUBLICATIONS

Choma et al., "Sensitivity advantage of swept source and Fourier domain optical coherence tomography," Optics Express, vol. 11, No. 18, pp. 2183-2189, Sep. 8, 2003.

(Continued)

*Primary Examiner* — Kenneth R Coulter
(74) *Attorney, Agent, or Firm* — Myers Bigel Sibley & Sajovec

(57) ABSTRACT

Optical coherence tomography (OCT) imaging systems for imaging an eye are provided including a source having an associated source arm path and a reference arm having an associated reference arm path coupled to the source path, the reference arm path having an associated reference arm path length. A sample having an associated sample arm path coupled to the source arm and reference arm paths is provided. A reference arm path length adjustment module is coupled to the reference arm. The reference arm path length adjustment module is configured to automatically adjust the reference arm path length such that the reference arm path length is based on an eye length of the subject. Related methods and computer program products are also provided.

36 Claims, 18 Drawing Sheets

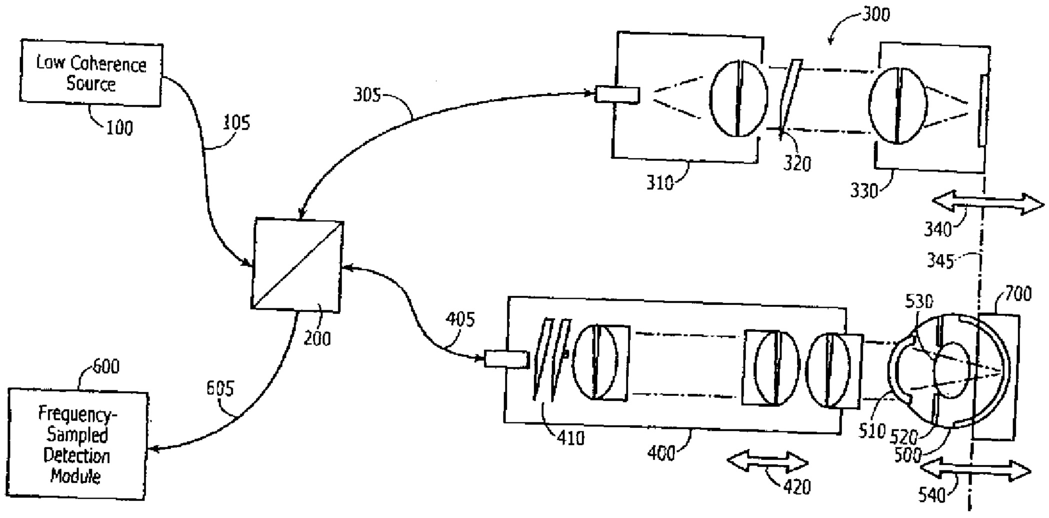

Pediatric Eye
Adult-optimized optics

Adult-Eye/
Pediatric-optimized optics

Pediatric Eye
Pediatric-optimized optics